United States Patent
Fowler et al.

(10) Patent No.: US 8,135,472 B2
(45) Date of Patent: Mar. 13, 2012

(54) SYSTEMS AND METHODS FOR TREATING AUTISM SPECTRUM DISORDERS (ASD) AND RELATED DYSFUNCTIONS

(75) Inventors: Brad C. Fowler, Duvall, WA (US); Dominic W. Massaro, Santa Cruz, CA (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 295 days.

(21) Appl. No.: 12/415,200

(22) Filed: Mar. 31, 2009

(65) Prior Publication Data

US 2009/0299126 A1 Dec. 3, 2009

Related U.S. Application Data

(60) Provisional application No. 61/057,144, filed on May 29, 2008.

(51) Int. Cl.
*A61N 2/00* (2006.01)
(52) U.S. Cl. ....... 607/45; 607/1; 607/2; 607/3; 607/115; 607/139; 600/9; 600/544; 600/545
(58) Field of Classification Search ................... 607/1–3, 607/45, 115, 139; 600/9, 544–545
See application file for complete search history.

(56) References Cited

U.S. PATENT DOCUMENTS

| | | | |
|---|---|---|---|
| 6,234,979 B1 | 5/2001 | Merzenich | |
| 7,225,129 B2 | 5/2007 | Massaro et al. | |
| 7,623,927 B2 | 11/2009 | Rezai | |
| 2006/0015153 A1* | 1/2006 | Gliner et al. | ............ 607/45 |
| 2007/0179558 A1 | 8/2007 | Gliner | |

OTHER PUBLICATIONS

Van Kooten, et al., "Neurons in the Fusiform Gyrus are Fewer and Smaller in Autism," Brain, Mar. 10, 2008, vol. 131m, pp. 987-999.
ISA/US, International Search Report for PCT/US2009/039032 dated Feb. 20, 2010.
Baer, D.M. et al., "Some Current Dimensions of Applied Behavior Analysis," Journal of Applied Behavior Analysis, No. 1, Spring 1968, pp. 91-97.
Berument, S.K. et al., "Autism Screening Questionaire: Diagnostic Validity," British Journal of Psychiatry, vol. 175, 1999, pp. 444-451.
Dawson, G. et al., "Neural Correlates of Face and Object Recognition in Young Children with Autism Spectrum Disorder, Developmental Delay, and Typical Development," Child Development, vol. 73, No. 3, 2002, pp. 700-717.
Massaro, D.W., "Perceiving Talking Faces: From Speech Perception to a Behavioral Principle," MIT Press, 1998, pp. 141-143.

(Continued)

*Primary Examiner* — Carl H Layno
*Assistant Examiner* — Deborah Malamud
(74) *Attorney, Agent, or Firm* — Christopher S. L. Crawford; Craig Hoersten; Peter R. Lando

(57) ABSTRACT

Systems and methods for treating autism spectrum disorders (ASD) and related dysfunctions are disclosed. A method in accordance with a particular embodiment includes determining that a patient suffers from an autistic disorder and, based at least in part on the determination, selecting a cortical signal delivery site. The method can further include implanting an electrode within the patient's skull and external to a cortical surface of the patient's brain, and treating the autistic disorder by applying electrical signals to the implanted electrode in conjunction administering an adjunctive therapy to the patient.

9 Claims, 18 Drawing Sheets

OTHER PUBLICATIONS

Massaro, D.W., "Symbiotic Value of an Embodied Agent in Language Learning," Hawaii International Conference on System Sciences, 2004, 10 pages.

Massaro, D.W. et al., "A Multilingual Embodied Conversational Agent," Hawaii International Conference on System Sciences, 2005, 8 pages.

Massaro, D.W. and Bosseler, A., "Perceiving Speech by Ear and Eye: Multimodal Integration by Children with Autism," Journal of Developmental and Learning Disorders, vol. 7, 2003, pp. 111-144.

Pierce, K. et al., "Face Processing Occurs Outside the Fusiform 'Face Area' in Autism: Evidence from Functional MRI," Brain, vol. 124, 2001, pp. 2059-2073.

Shams, L. et al., "What You See is What You Hear," Nature, vol. 408, 2000, p. 788.

Snowling, M. and Frith, U., "Comprehension in 'Hyperlexic' Readers," Journal of Experimental Child Psychology, vol. 42, 1986, pp. 392-415.

Spencer, P.E. and Marschark, M., "Spoken Language Development of Deaf and Hard-of-Hearing Children," Oxford University Press, 2006, pp. 212-243.

Tager-Flusberg, H., "A Psychological Approach to Understanding the Social and Language Impairments in Autism," for International Review of Psychiatry, manuscript revised Jun. 14, 1999, 37 pages.

Violentyev, A. et al., "Touch-Induced Visual Illusion," NeuroReport, vol. 16, No. 10, 2005, pp. 1107-1110.

Williams, J.H.G. et al., "Imitation, Mirror Neurons and Autism," to appear in Neuroscience and Behavioral Reviews, 28 pages.

Williams, J.H.G. et al., "Visual-Auditory Integration During Speech Imitation in Autism," Research in Developmental Disabilities, vol. 25, 2004, pp. 559-575.

Zilbovicius, M. et al., "Austim: Neuroimaging," Rev Bras Psiquiatr, vol. 28, 2006, pp. S21-S28.

Zilbovicius, M. et al., "Temporal Lobe Dysfunction in Childhood Autism: A PET Study," Am J Psychiatry, 157:12, 2000, pp. 1988-1993.

\* cited by examiner

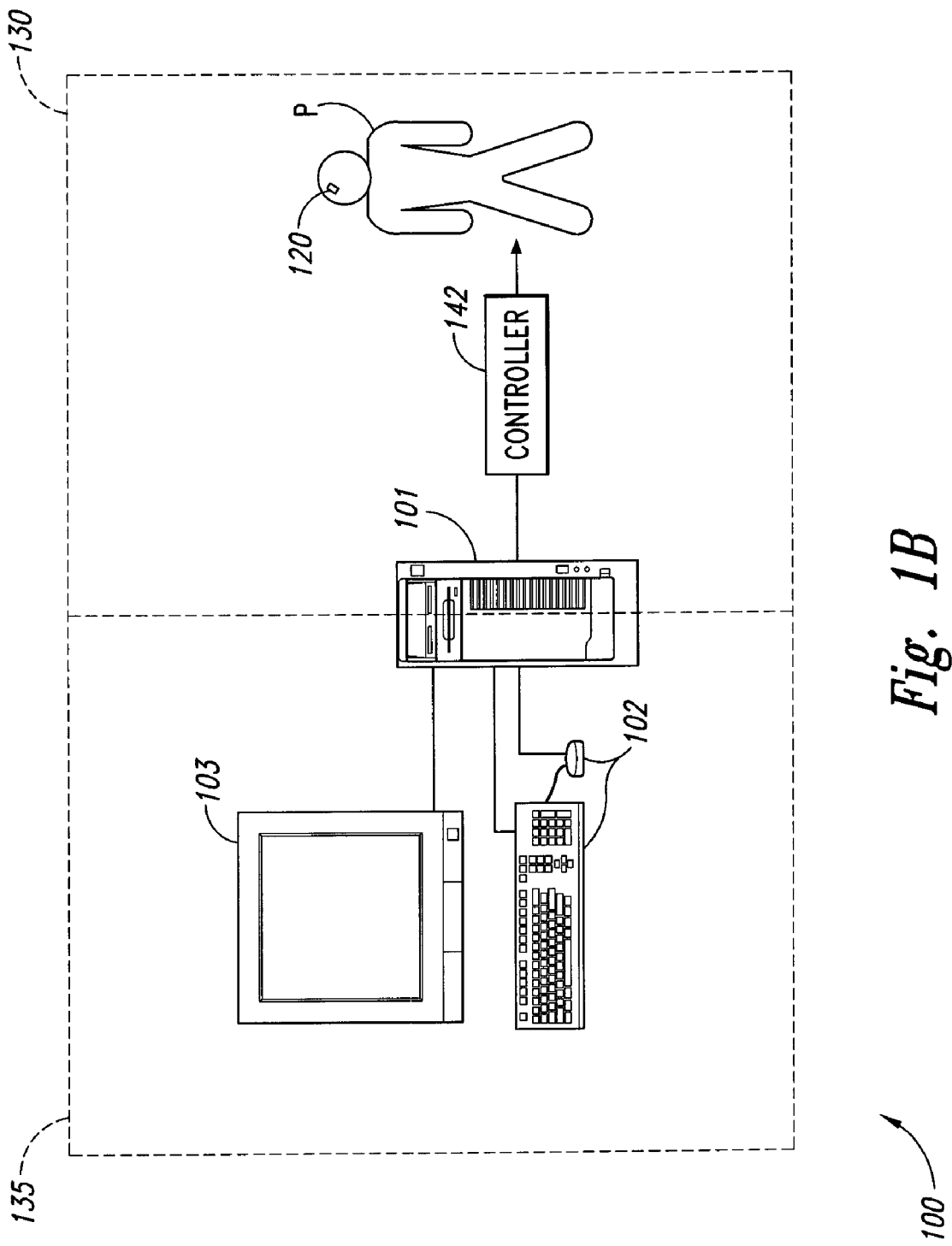

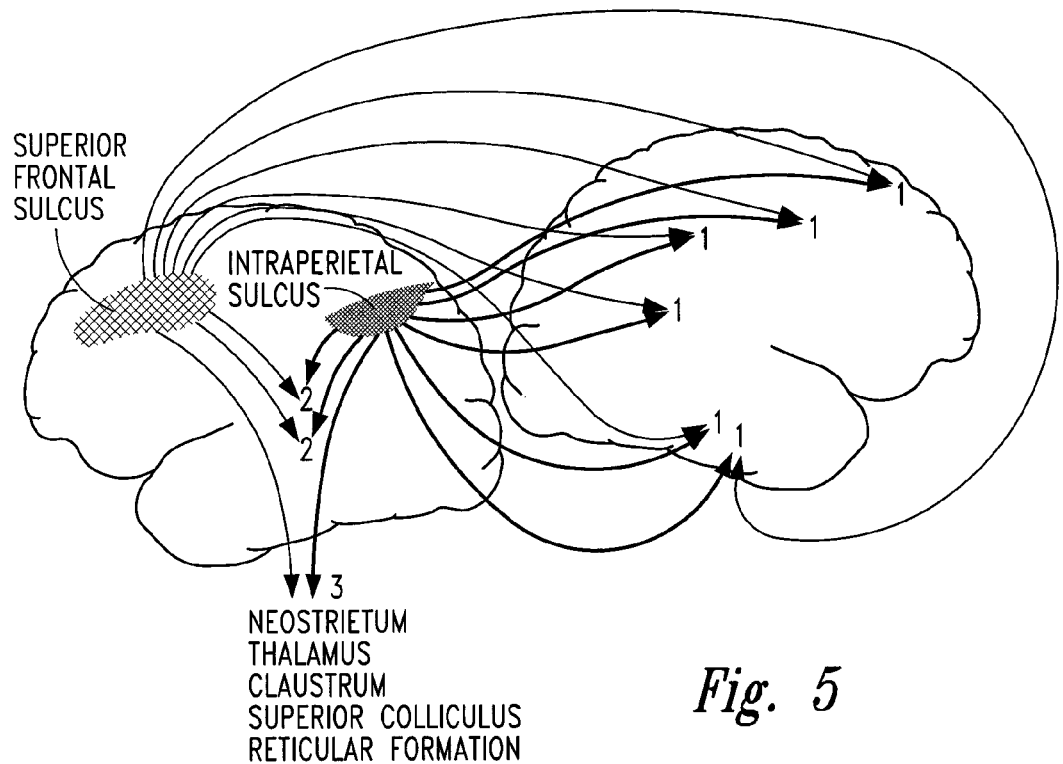
*Fig. 5*
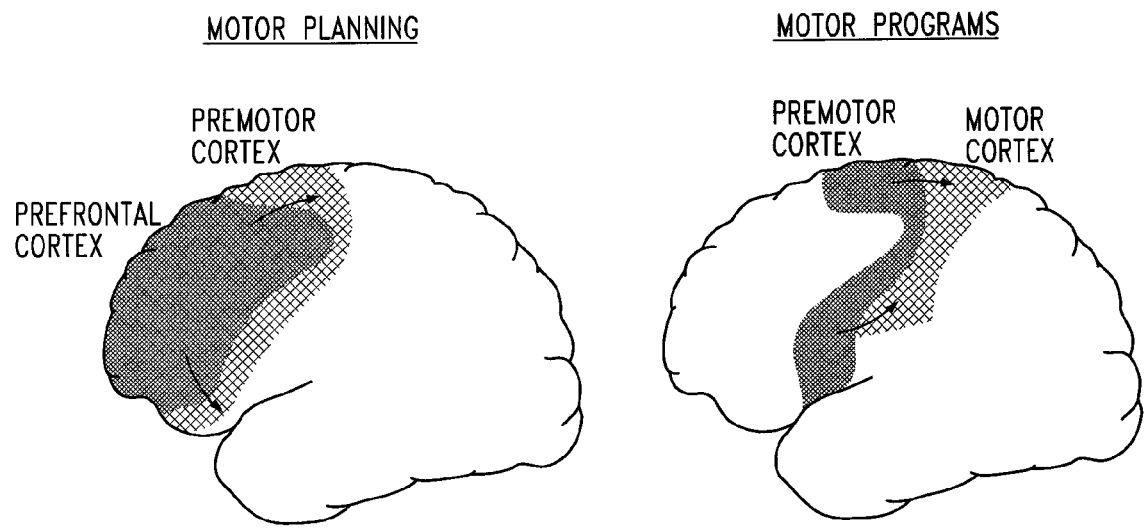
*Fig. 6A*  *Fig. 6B*

HAPPY    ANGRY    SURPRISED    FEARFUL

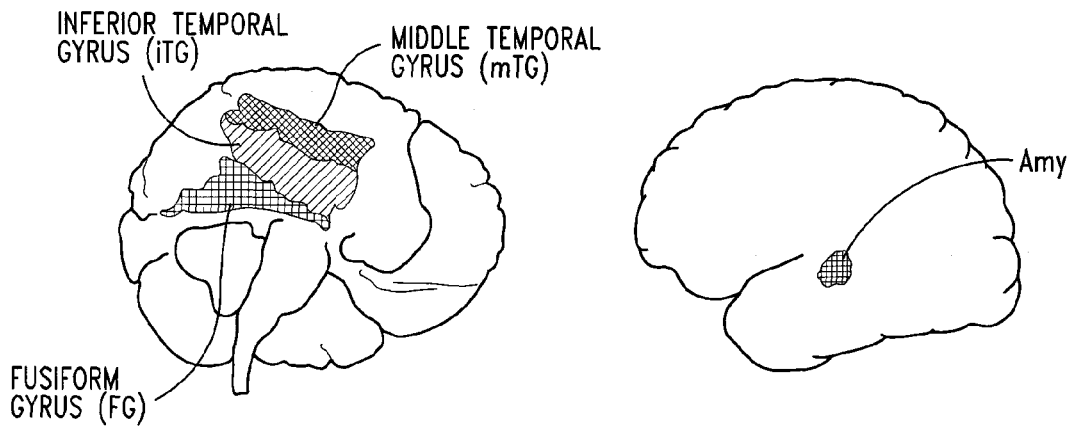
*Fig. 18A*  *Fig. 18D*
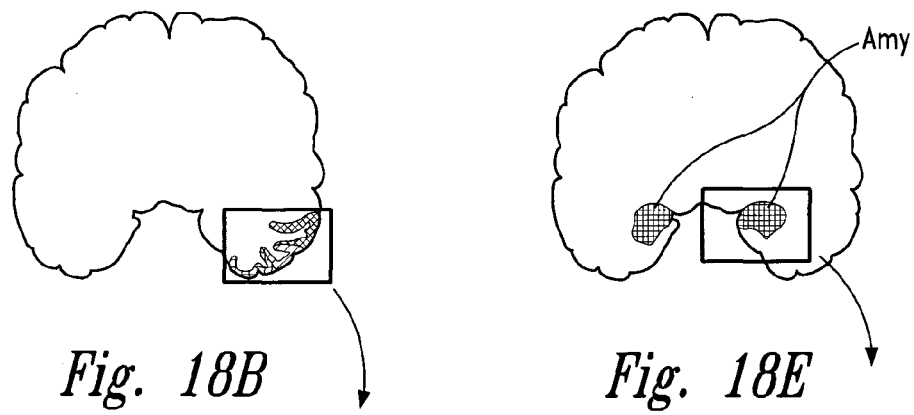
*Fig. 18B*  *Fig. 18E*
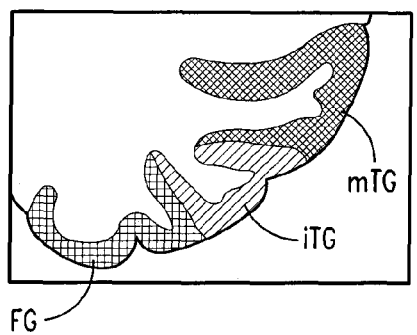  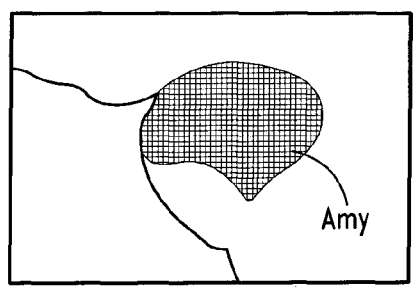
*Fig. 18C*  *Fig. 18F* under the heading of, "SYSTEMS AND METHODS FOR TREATING AUTISM SPECTRUM DISORDERS (ASD) AND RELATED DYSFUNCTIONS", with page number US 8,135,472 B2.

SYSTEMS AND METHODS FOR TREATING AUTISM SPECTRUM DISORDERS (ASD) AND RELATED DYSFUNCTIONS

CROSS-REFERENCE TO RELATED APPLICATION

The present application claims priority to U.S. Provisional Application No. 61/057,144 filed May 29, 2008 and incorporated herein by reference.

TECHNICAL FIELD

Aspects of the present disclosure are directed generally toward systems and methods for treating autism spectrum disorders (ASD) and related dysfunctions.

BACKGROUND

The Autism Spectrum Disorders (ASD) range from a mild form called Asperger syndrome to more severe forms—autistic disorder, Rett syndrome and childhood disintegrative disorder. ASD is characterized by deficits in social interaction and verbal and nonverbal communication. Stereotyped, repetitive behaviors like hand flapping or head banging are common in more severe cases. It has been claimed that deficits in imitation and empathy suggest that there is an underlying deficiency in the "theory of mind," which is the ability to understand that others have beliefs, desires and intentions that are different from one's own.

ASD can be detected as early as 12 to 18 months but often is not diagnosed until the age of 3 years. Autism currently affects 0.34% of children between the ages of 3 and 10 years old. ASD is a developmental disorder and in many cases, early detection is important so that intervention can begin at a young age. Existing treatments include behavioral therapies that focus on developing communication and social interaction skills. Medications are available to treat behavioral problems, e.g., selective serotonin reuptake inhibitors (SSRIs) for anxiety and depression, and antipsychotic medications for severe behavioral problems. Anticonvulsants are used to treat seizures, and stimulants are used to treat inattention and hyperactivity. The pathology of ASD is poorly understood and it does not appear that any of these medications treat the underlying causes. Accordingly, there is a need for improved ASD treatments and associated treatment systems.

BRIEF DESCRIPTION OF THE DRAWINGS

FIG. 1B is a schematic diagram of a system in accordance with an embodiment of the disclosure.

FIG. 5 illustrates the prefrontal and parietal association areas and interconnections between these areas.

FIGS. 6A-6B illustrate the flow of information in the motor control system.

FIGS. 18A-18F illustrate representative target neural populations for stimulation in accordance with particular embodiments.

DETAILED DESCRIPTION

Aspects of the present disclosure are directed generally to systems and methods for treating autism spectrum disorders (ASD) and related dysfunctions. In general, representative methods can include identifying suitable target sites, applying electromagnetic signals and/or other treatment modalities at the target sites, and, in at least some instances, administering an adjunctive therapy in conjunction with the applied signals. Several details describing structures and processes that are well known and often associated with such systems and methods are not set forth in the following description for purposes of brevity. Moreover, although the following disclosure sets forth several representative embodiments of systems and methods for treating ASD, several other embodiments can have different configurations and/or different components than those described in this section. Accordingly, such embodiments may include additional elements and/or may eliminate one or more of the elements described below with reference to FIGS. 1A-23.

Overview

Figure 1A:
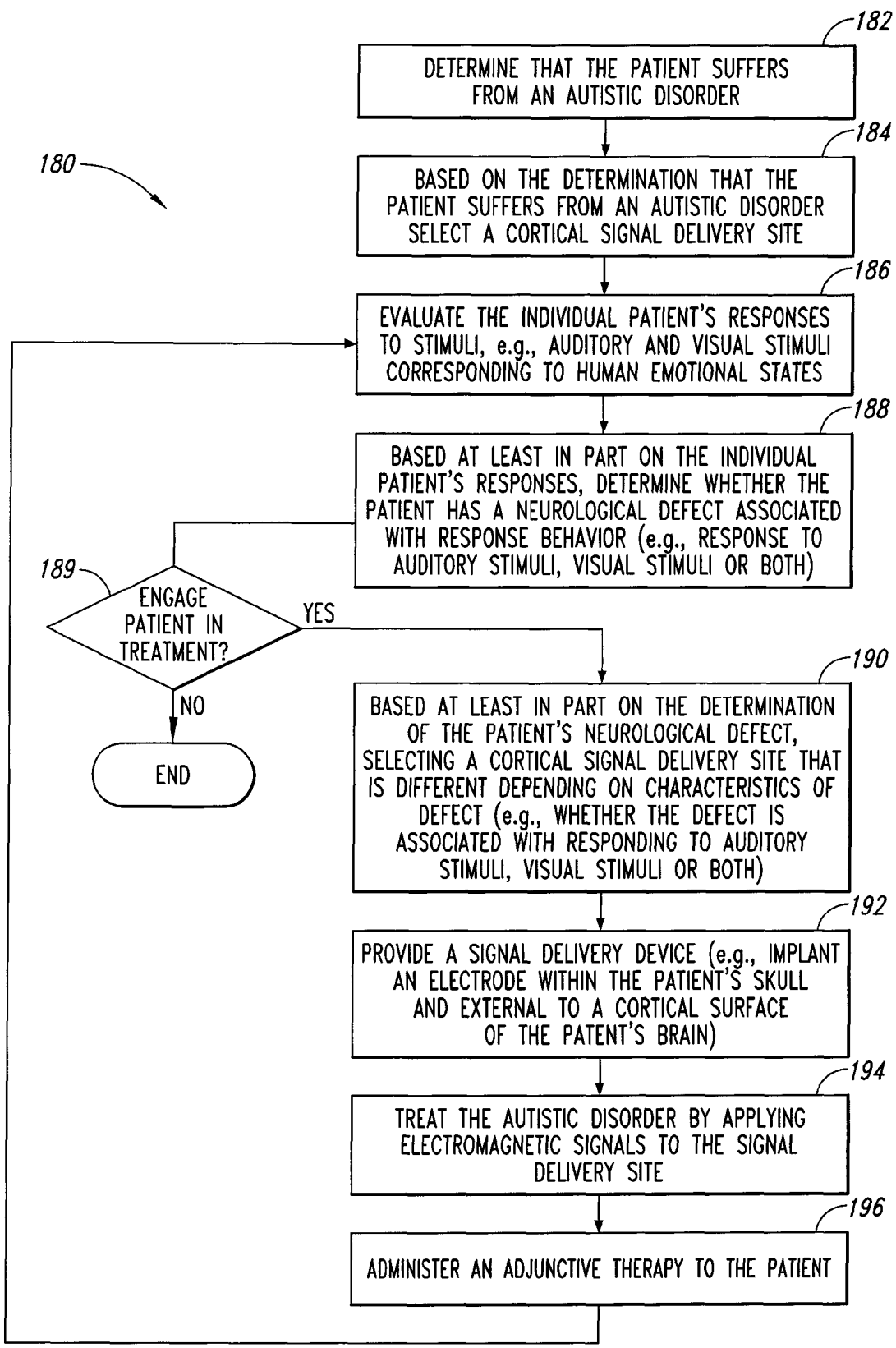
FIG. 1A is a block diagram illustrating a representative method in accordance with an embodiment of the disclosure.

FIG. 1A is a flow diagram illustrating a representative process 180 in accordance with an embodiment of the disclosure. The process 180 can include determining that a patient suffers from an autistic disorder (e.g., ASD), as identified in process portion 182. This determination can be made, for example, on the basis of patient responses to testing and/or specific symptoms exhibited by the patient. Process portion 184 can include selecting a cortical signal delivery site, based (at least in part) on the determination that the patient suffers from an autistic disorder. Selecting the cortical signal delivery site can include an evaluation and analysis process. For example, as shown in process portion 186, the process can include evaluating the patient's responses to one or more stimuli, e.g., auditory and visual stimuli corresponding to human emotional states. The patient evaluation can include, in addition to assessing the patient's performance on tests, reviewing the patient's history for details of specific symptoms or sets of symptoms, and identifying the most severe and/or debilitating symptoms.

Process portion 188 includes, based at least in part on the individual patient's responses to one or more selected stimuli, determining whether the patient has a neurological defect associated with the response behavior. For example, the defect can be associated with a patient's response to auditory stimuli, visual stimuli, or both. Process portion 189 includes determining whether to engage the patient in treatment (e.g., a new treatment regimen or a revised treatment regimen). In process portion 190, the process includes, based at least in part on the determination of the patient's neurological defect, selecting a cortical signal delivery site that is different depending on the characteristics of the defect. For example, the cortical signal delivery site can be different depending upon whether the defect is associated with the patient's response to and/or processing of auditory stimuli, visual stimuli, or both. Process portion 190 can include acquiring functional imaging data during appropriate behavioral tests, for example, responses to the stimuli corresponding to human emotional states. In other embodiments, electrophysiological data can be collected with scalp electrodes and analyzed, instead of or in addition to performing functional imaging. For example, a localized desynchronization of EEG activity can be used to identify hypoactive neural populations. In other embodiments, a power decrease in the EEG spectrum or changes in coherence can be indicative of hypoactivity or other neurological defects.

In process portion 192, a signal delivery device is provided to address the neurological defect. For example, the signal delivery device can include an electrode implanted within the patient's skull and external to the cortical surface of the patient's brain. In process portion 194, the autistic disorder is treated by applying electromagnetic signals to the signal delivery site. In particular embodiments, the signals are applied in conjunction with administering an adjunctive therapy to the patient, for example, a behavioral therapy (process portion 196). The process 180 can then return to process portion 186 for a re-evaluation of the patient. The practitioner can continue the patient treatment if warranted by the evaluation performed in process portions 186 and 189, and if not, the process 180 can end. For example, if the patient has responded favorably to the treatment regimen, but the patient's response has stabilized, the treatment (e.g., the stimulation, possibly augmented by behavioral therapy) can be concluded.

As used herein, the term "stimulation" is used generally to include electromagnetic signals applied to a target neural population. Accordingly, the signals can include electrical signals applied to the patient's brain via a cortical implant, (e.g., cortical stimulation, or CS), a deep brain implant (e.g., deep brain stimulation, or DBS), and/or a transcranial technique (e.g., transcranial direct current stimulation or tDCS). Magnetic signals can be applied transcranially using repetitive transcranial magnetic stimulation or rTMS. Though generally referred to as "stimulation," the signals may have direct or indirect facilitatory effects, inhibitory effects, and/or plasticity-enhancing effects, as will be described further later.

FIG. 1B is a schematic illustration of a system 100 that can be used to evaluate and/or treat a patient P in accordance with several embodiments of the disclosure. The system 100 can include an evaluation/adjunctive therapy system 135 and a signal delivery system 130. Aspects of both systems 130, 135 can be controlled at least in part by a processor 101. The processor 101 can be a single shared processor, or separate processors can be provided for each of the signal delivery system 130 and the evaluation/adjunctive therapy system 135. The evaluation/adjunctive therapy system 135 can further include input devices 102 and one or more output devices 103 that are operated by a practitioner, therapist, and/or the patient to provide data regarding the patient's dysfunctions before, during, and/or after treatment. Information received during one or more evaluation processes can be used by the practitioner and, in at least some instances, automatically by the system 100 to initiate, control, and/or update the therapy provided to the patient P. The therapy provided to the patient P is provided by a signal delivery device 120 (e.g., an implanted or non-implanted electromagnetic stimulator) that is under the control of a controller 142. The overall system 100 can be operated in an open-loop format to provide initial and/or updated treatment regimens, or the patient (generally with assistance from a practitioner) can provide responses via the input devices 102 that are then automatically used to update the signals directed from the controller 142 to the signal delivery device 120, in a closed-loop format.

Representative Brain Functions

Brain imaging studies have implicated a number of cortical and subcortical regions that may play a role in ASD. Structural imaging and postmortem studies have reported increased total brain volume in autistic patients. The cerebellum has been extensively investigated in autistic patients, but early findings have not always been replicated. Other studies have reported anatomic anomalies in the corpus callosum, amygdala, hippocampus and cingulate cortex, but again, it has not always been possible to replicate these findings. Significant decreases in gray matter within the temporal lobes have been reported, especially in and around the superior temporal gyrus. This last finding is consistent with functional imaging studies discussed below.

Functional imaging studies (as compared with structural imaging studies) have also identified a number of regions that may potentially contribute to autism. Positron emission tomography (PET) and functional magnetic resonance imaging (fMRI) studies reveal decreased levels of activity in much of the prefrontal region—e.g., Brodmann areas 9, 10, 11, 12, 44, 45, and 46. Metabolic reductions have also been observed in the cingulate cortex and amygdala, which presumably relates to the flat affect and inappropriate emotional responses exhibited by autistic patients. The temporal lobes exhibit a highly significant hypometabolism in PET and SPECT imaging. Any one or combination of these cortical areas are candidates for stimulation (e.g., electromagnetic stimulation) in the treatment of autism. In one embodiment of this disclosure, electromagnetic signals are applied to the cortex to increase the activity in any and/or all of these regions, because functional imaging studies repeatedly report hypoactivity in ASD patients, as compared to normal subjects. However, these cortical regions encompass much of the prefrontal and temporal lobes, and it is not practical to target such a large cortical region with electromagnetic stimulation. Accordingly, certain embodiments of the present disclosure are directed to identifying target area(s) for treating autism with greater specificity, so as to improve the efficiency and/or efficacy of the treatment.

The symptomology of autism and the involved cortical regions described above suggest that the so-called executive functions have been compromised in autistic patients. These functions include interpreting sensory information, associating perceptions with previous experience, focusing attention, planning actions, and other cognitive functions responsible for organizing appropriate motor responses to incoming sensory inputs. Many of these executive functions are also critical components of the social brain network, which may explain the social impairments seen in even mild cases of autism or Asperger syndrome. Accordingly, aspects of the present disclosure include identifying the target areas for receiving electrical and/or other forms of stimulation, based at least in part on the architecture of executive functioning in the human brain, which is briefly summarized below.

The brain can be viewed as a structure responsible for organizing and implementing appropriate motor responses to incoming sensory stimuli. Visual, auditory and somatosensory inputs enter the cortex at primary processing centers in the occipital, temporal and parietal lobes, respectively. FIGS. 2-6 are schematic representations of the brain, illustrating selected neural pathways, based on information described by Eric Kandel et al. in "Principals of Neuroscience," 4th Ed. (2000). FIGS. 2-6 are provided to illustrate the general principals associated with these pathways—for purposes of illustration, clarity and brevity, particular details of these pathways known to those of ordinary skill in the relevant art are not shown in FIGS. 2-6.

Figure 2:
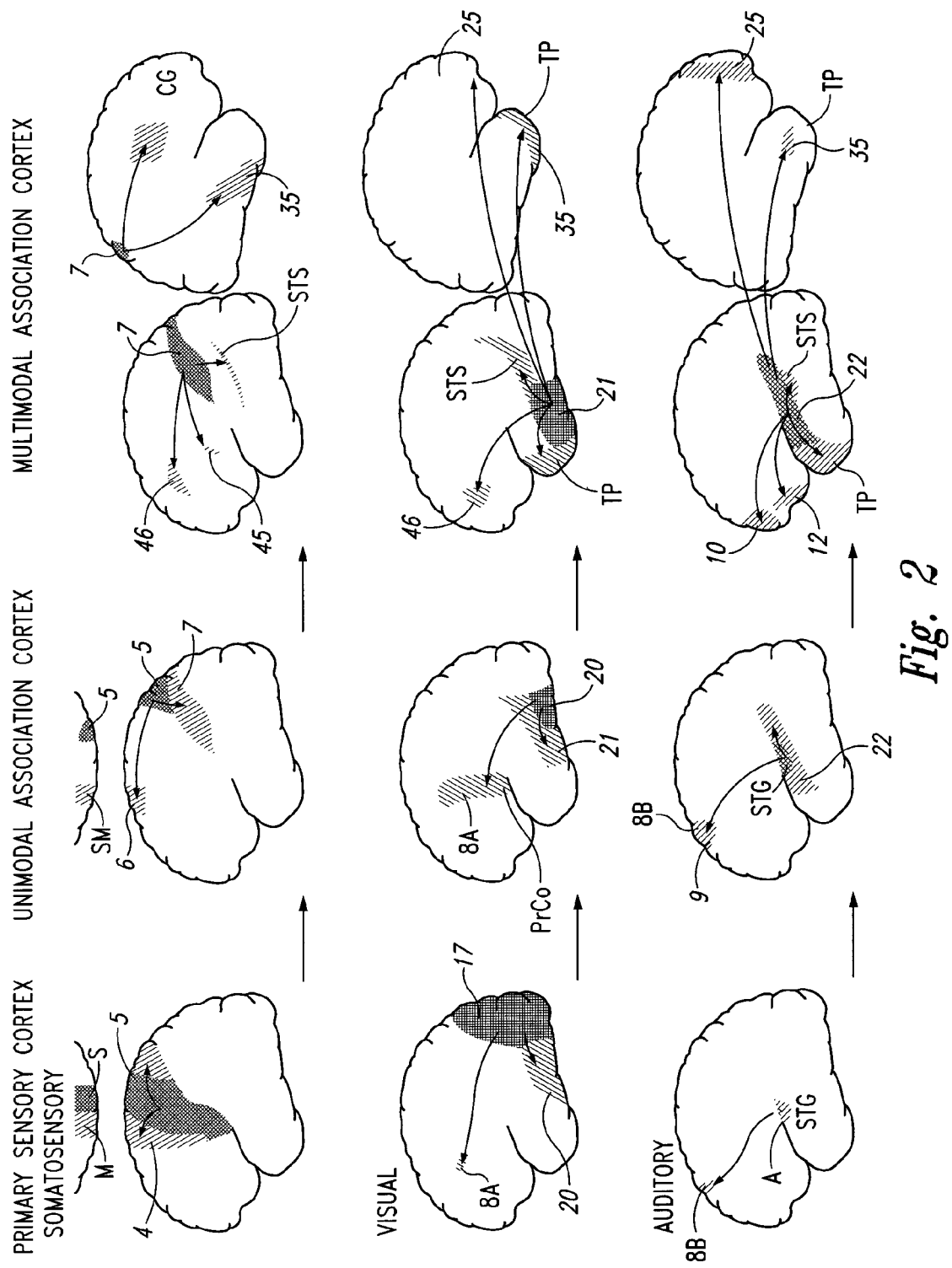
FIG. 2 illustrates pathways to the somatosensory, visual and auditory association areas.

FIG. 2 illustrates representative brain structures, Brodmann areas, and pathways to the somatosensory, visual and auditory association areas. As shown in FIG. 2, hierarchical connections between cortical areas progress from the primary sensory cortex to the unimodal association cortex to the multimodal association cortex. At each stage, progressively more abstract information is extracted from the sensory stimulus and is projected to the next stage, as is discussed further below.

Figure 3:
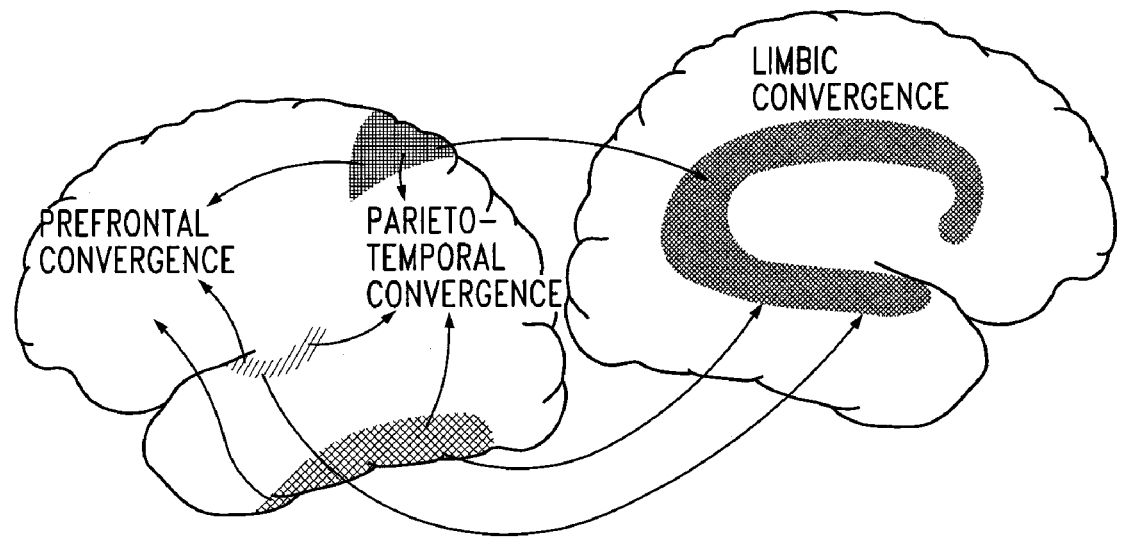
FIG. 3 illustrates unimodal sensory inputs converging on multimodal association areas in the prefrontal, parietotemporal, and limbic cortecies.

Each of the primary sensory processing areas identified above is unimodal—that is, these areas primarily receive and process neural activity associated with one sensory modality. Each of these primary sensory regions processes specific aspects of the sensory input, and then passes it along to secondary sensory regions (unimodal association cortices) that process more complex aspects of the input. These secondary sensory regions then project to multimodal regions in the prefrontal, parietotemporal, and limbic cortices where the different sensory modalities are combined to create an integrated sensation or representation of the stimulus. FIG. 3 illustrates unimodal sensory inputs converging on multimodal association areas in the prefrontal, parietotemporal, and limbic cortices where internal representations of the sensory stimulus are assembled.

Figure 4:
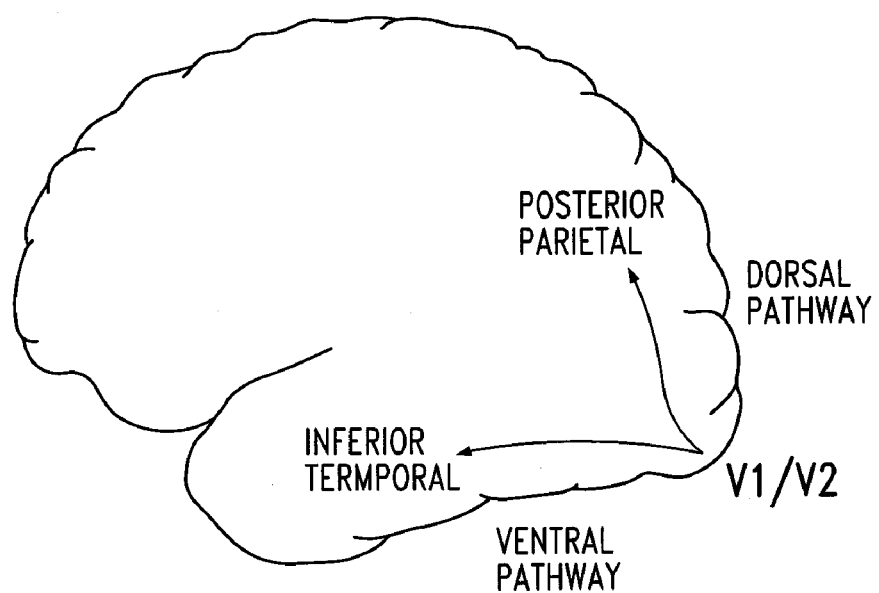
FIG. 4 illustrates the flow of sensory information at dorsal and ventral pathways.

Along the foregoing pathway, the flow of sensory information is divided between dorsal and ventral pathways. As shown in FIG. 4, the dorsal pathway processes sensory information (e.g., depth and motion) relating to where objects are located. The ventral pathway processes sensory information (e.g., color, shape and form) relating to what the objects are. As shown in FIG. 5, the multimodal association areas project to and are interconnected with two "central processors": the anterior association cortex (e.g., the dorsolateral prefrontal cortex—DLPFC, or superior frontal sulcus) and the parietal association cortex (or intra-parietal sulcus) that are also heavily interconnected. An integrated representation of the constantly changing world is generated in the parietal area, while the prefrontal area constructs a representation of our body moving in and manipulating this world. It has been suggested that the conscious sense of a coherent self emerges from the operation of these two association cortices. This suggestion is supported by evidence indicating that lesions in either region result in selective and restrictive loss of self-awareness for certain types of stimuli, while maintaining awareness for others. As noted above, the parietal association cortex provides an integrated perception of the constantly changing world around us while the anterior association cortex puts our self-image in that world so that we can manipulate it. It is in the interactions between these two cortical regions that appropriate motor responses are selected for incoming stimuli.

The amygdala and cingulate cortex provide emotions and memories gained from previous experience to guide the selection of appropriate motor responses. As shown in FIGS. 6A and 6B, the selected response is defined in very general terms initially in the prefrontal cortex but becomes more specific as the flow of neural activity spreads into the motor control system. The prefrontal cortex selects specific motor responses and generates motor plans, which are projected to the premotor cortex (as shown in FIG. 6A). The premotor cortex in turn generates the motor program or specific sequence of motor actions (FIG. 6B). Finally, neurons in the primary motor cortex activate movements to implement the motor response.

The foregoing network is complex and not always well understood. Accordingly, it is not always readily apparent where the lesion creating the ASD occurs. It is also not clear if lesions creating similar ASDs in different patients are located at the same or different anatomical sites. It may not be clear whether the anomalous activities recorded in functional imaging are indicative of the etiological "source", or of secondary effects at "downstream" sites. In addition, once a suitable target site has been identified, the proper stimulation parameters must be selected to reduce symptoms and/or facilitate recovery from this debilitating disorder. Embodiments of the representative methods, described in further detail below, are directed at dealing with the foregoing uncertainties.

Imaging studies of ASD patients reveal anomalous activity levels (generally hypoactivity) in many of the cortical regions involved in executive functions. As noted above, symptoms can also vary widely between patients. Some patients are hypersensitive to certain sounds, while other patients are hypersensitive to visual stimuli. Some patients have better verbal skills than non-verbal skills, while other patients have better non-verbal skills. This inter-patient variability strongly suggests that the lesion(s) can be in any of these cortical areas, and that the lesion(s) can be in different locations in different patients. As implied by the name, ASD is a spectrum of disorders with a wide range of symptoms that reflect variability in the affected cortical components.

It could be argued that the primary "lesion" or affected cortical region is the ideal target for stimulation, and that an effective therapeutic stimulation at this site will cascade through downstream sites to normalize activity levels there as well. However, it may be difficult to differentiate between the "primary" lesion and other cortical sites secondarily affected by input from the primary lesion. At lower levels in the sensory/motor flow of neural activity, there is a predominant directionality so that primary sites can be identified as the "upstream" sites. Thus, for example, if hypoactivity is found in both the secondary auditory cortex and the parietotemporal multimodal association area, it may be inferred that the primary lesion is in the secondary auditory cortex. However, at the higher levels, cortical areas become increasingly interconnected and less hierarchical, making it more difficult to identify the "primary" lesion site. Accordingly, certain embodiments of the disclosed method include obtaining a detailed characterization of each patient's symptoms, along with an imaging analysis of the patient's affected cortical regions, so as to identify the "primary" site. Specific target sites can be selected, in part, by considering which symptoms most adversely affect the patient, and which component(s) of the executive neural circuitry are most likely involved. In general, once a "primary" site has been identified, stimulation can be directed to the primary site. If it is later determined (e.g., via a follow-up evaluation) that the deficit at the primary site has been addressed, and that a deficit now exists (or still exists) at a secondary site, then the stimulation can be directed to the secondary site during an additional or further treatment regimen.

Representative Stimulation Methodologies

Figure 7A:
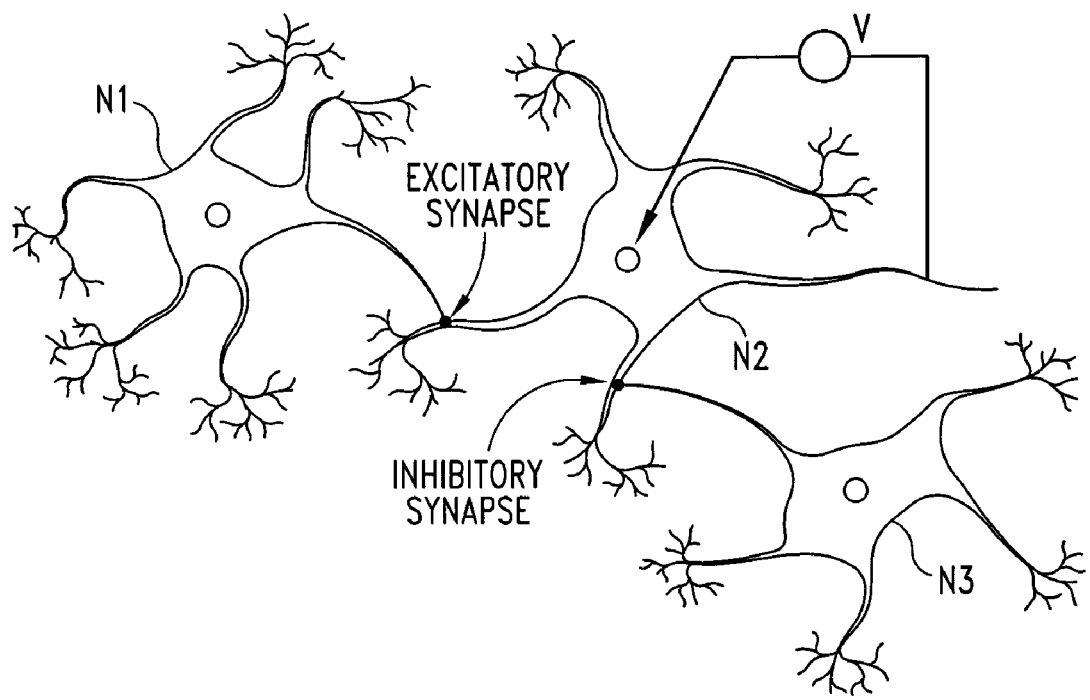
FIG. 7A is a schematic illustration of selected neurons.
Figure 7B:
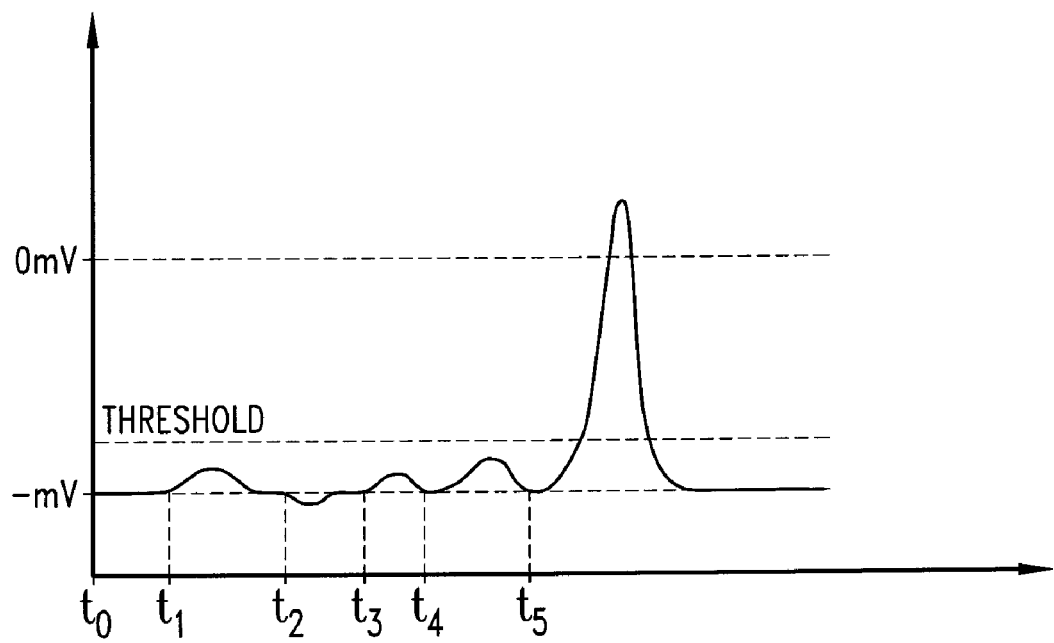
FIG. 7B is a graph illustrating the firing of an "action potential" associated with normal neural activity.

FIG. 7A is a schematic representation of several neurons N1-N3 and FIG. 7B is a graph illustrating an "action potential" related to neural activity in a normal neuron. Neural activity is governed by electrical impulses generated in neurons. For example, neuron N1 can send excitatory inputs to neuron N2 (e.g., at times $t_1$, $t_3$ and $t_4$ in FIG. 7B), and neuron N3 can send inhibitory inputs to neuron N2 (e.g., at time $t_2$ in FIG. 7B). The neurons receive/send excitatory and inhibitory inputs from/to a population of other neurons. The excitatory and inhibitory inputs can produce "action potentials" in the neurons, which are electrical pulses that travel through neurons by changing the flux of sodium (Na) and potassium (K) ions across the cell membrane. An action potential occurs when the resting membrane potential of the neuron surpasses a threshold level. When this threshold level is reached, an "all-or-nothing" action potential is generated. For example, as shown in FIG. 7B, the excitatory input at time t5 causes neuron N2 to "fire" an action potential because the input exceeds the threshold level for generating the action potential. The action potentials propagate down the length of the axon (the long process of the neuron that makes up nerves or neuronal tracts) to cause the release of neurotransmitters from that neuron that will further influence adjacent neurons.

Figure 7C:
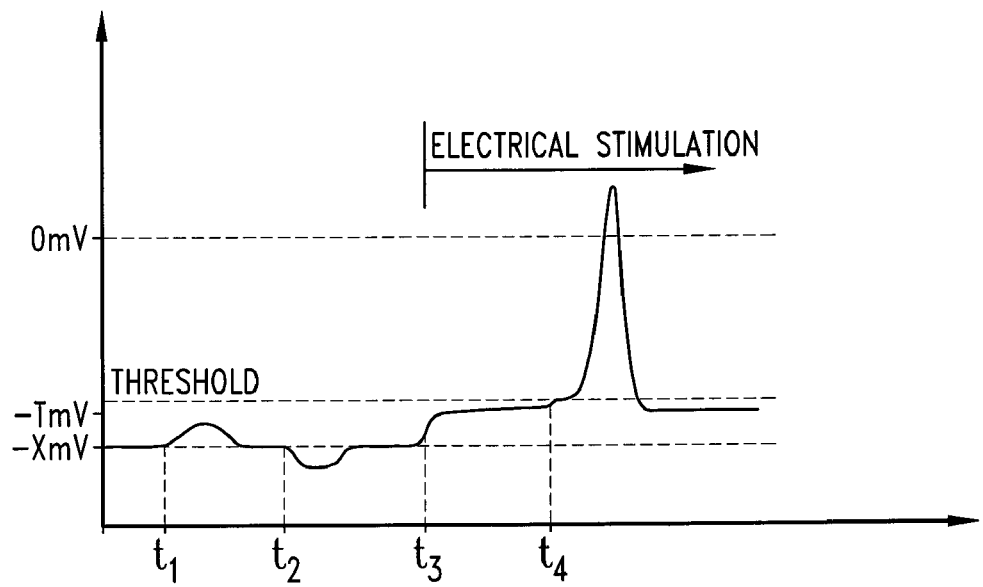
FIG. 7C is a graph illustrating firing and "action potential" associated with neural activity affected by a method in accordance with an embodiment of the disclosure.

FIG. 7C is a graph illustrating the application of a subthreshold potential to the neurons N1-N3 initially shown in FIG. 7A. At times $t_1$ and $t_2$, the depolarization waves generated in response to the intrinsic excitatory/inhibitory inputs from other neurons do not summate in a manner that "bridges-the-gap" from a neural resting potential at −X mV (e.g., approximately −70 mV) to a threshold firing potential at −T mV (e.g., approximately −50 mV). At time $t_3$, extrinsic electrical stimulation is applied to the brain, in this case at an intensity or level that is expected to augment or increase the magnitude of descending depolarization waves generated by the dendrites, yet below an intensity or level that by itself will be sufficient to summate in a manner that induces action potentials and triggers the neural function corresponding to these neurons. Extrinsic stimulation signals applied in this manner may generally be referred to as subthreshold signals. At time $t_4$, the neurons receive another excitatory input. In association with a set of appropriately applied extrinsic stimulation signals, even a small additional intrinsic input may result in an increased likelihood that a summation of the descending depolarization waves generated by the dendrites will be sufficient to exceed the difference between the neural resting potential and the threshold firing potential to induce action potentials in these neurons. Thus, in this situation, the subthreshold extrinsic signals facilitate the generation of action potentials in response to intrinsically occurring neural signaling processes. It is to be understood that depending upon signal parameters, the extrinsic signals may exert an opposite (disfacilitatory, inhibitory, or disruptive) effect upon neurons or neural signaling processes, and hence particular signal parameters may be selected in accordance with a likelihood of achieving a desired or intended therapeutic effect or outcome at any given time.

The actual signal(s) applied by one or more extrinsic signal delivery devices positioned in, upon, or above the brain to achieve a therapeutic or intended effect will vary according to the individual patient, the type of therapy, the type of electrodes (or other signal delivery device), and/or other factors. In general, the pulse form(s) of the electromagnetic signals (e.g., the frequency, pulse width, waveform, current level, and/or voltage) directed toward achieving an intended therapeutic effect may be selected or estimated relative to a test signal level or intensity at which a neural function is triggered or activated, or a change in a physiologic parameter (e.g., cerebral blood flow) is detected. Additionally or alternatively, the pulse form(s) of the first and/or second electromagnetic signals may be selected, adjusted, modulated, limited, or constrained at one or more times relative to parameters corresponding to one or more previously (e.g., most-recently) applied signals, or a maximum allowable or intended peak or average stimulation signal intensity.

In one embodiment of this disclosure, stimulation is applied to facilitate plasticity and reorganization of the affected cortex. In this embodiment, cortical stimulation can be coupled with behavioral cognitive therapies designed to ameliorate the selected symptoms. In particular embodiments, signal delivery parameters may be generally similar to those expected (based on studies performed by the assignee of the present application) to be beneficial for treating other dysfunctions, including but not limited to stoke. For example, in a particular embodiment, cathodal electrical signals are applied to a target neural population at a frequency of from about 50 Hz to about 150 Hz (e.g., about 100 Hz), a pulse width of from about 50 microseconds to about 250 microseconds (e.g., about 100 microseconds), and an amplitude (current or voltage) of from about 25% to about 50% (e.g., about 40%) of the activation threshold level for neurons at the target neural population. Depending on the patient's needs, behavioral therapies can include social interactions and/or communication exercises designed to improve these skills. Further details of representative therapies are discussed later.

In another embodiment, cortical stimulation can be applied to change the activity levels in areas found to exhibit anomalous activity levels in the patient (e.g., to alter the excitability of target neural populations). Typically, ASD patients have regions of hypoactivity compared to normal subjects, and the stimulation can accordingly be used to increase this neural activity. This embodiment does not necessarily combine behavioral therapies with the cortical stimulation (unlike the preceding embodiment) because this treatment is focused more on changing neural activity levels rather than promoting cortical reorganization. In a particular embodiment, assuming a hypoactive target neural population, anodal electrical signals are applied at a frequency of from about 75 Hz to about 150 Hz (e.g., about 100 Hz), a pulse width of from about 50 microseconds (e.g., about 100 microseconds) and an amplitude (current or voltage) of from about 25% to about 60% (e.g., about 50%) of the activation threshold level for neurons at the target neural population. If the target neural population is hyperactive, the practitioner can apply cathodal electrical signals to inhibit the target neural population, for example, at a frequency of from about 75 Hz to about 150 Hz (e.g., about 100 Hz), a pulse width of from about 50 microseconds to about 250 microseconds (e.g., about 100 microseconds), and an amplitude (current or voltage) of from about 50% to about 75% (e.g., about 60%) of the activation threshold level for neurons at the target neural population. If rTMS techniques (rather than direct cortical stimulation techniques) are used to affect neural activity levels, the practitioner can select rTMS frequencies of 5-10 Hz and above to treat a hypoactive neural population, or less than 5 Hz to treat a hyperactive neural population.

Representative Stimulation Systems

As discussed above, direct cortical stimulation can be used to treat patients for ASD in many cases. As was also discussed earlier, ASD in many cases emerges in the first few years of life, leaving the patient with life-long impairments in social and communication skills. Accordingly, it may be desirable to apply stimulation to the patient before the critical period of developing these skills has passed. However, it is generally unlikely that infants will be implanted with cortical stimulation electrodes because the infant's head grows so rapidly that it may be difficult to maintain proper electrode positioning over the course of a treatment regimen. Accordingly, other delivery modalities (e.g., rTMS) may be used for younger patients, and/or in situations in which an implanted electrode is not as suitable for the patient. Implanted electrodes can be used for teenagers, young adults, and/or other patients more suited to the use of such electrodes.

Figure 8A:
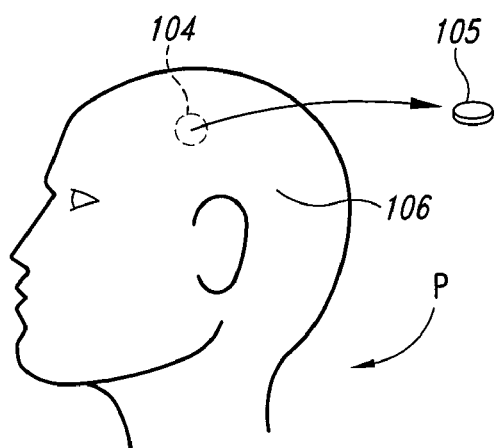
FIGS. 8A and 8B are schematic illustrations of an implanting procedure in accordance with an embodiment of the disclosure.
Figure 8B:
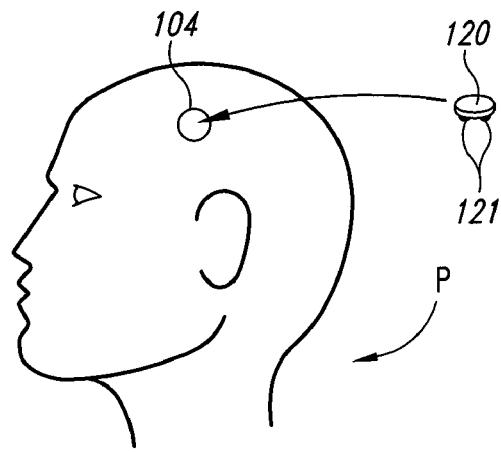

In a representative example, the applied electromagnetic signals described above are delivered by an implanted signal delivery device, shown schematically in FIGS. 8A-8B. Referring first to FIG. 8A, a skull section 105 is removed from a patient P adjacent to one or more target neural populations (a single target neural population 104 is shown in FIG. 8A for purposes of illustration). The skull section 105 can be removed by boring a hole in the skull 106 in a manner known in the relevant art, or a much smaller hole can be formed in the skull 106 using drilling techniques that are also known in the art. The hole can be 0.2-4.0 cm in diameter in a particular embodiment, but can have other dimensions depending upon factors that include the size (and/or number) of the target neural population(s), and/or the size of the implanted device.

Referring to FIG. 8B, an implantable signal delivery device 120 having first and second electrodes or contacts 121 can then be implanted in the patient P. The contacts 121 can be positioned at or close to the target neural population for bipolar stimulation (as shown in FIG. 8B), or for other types of multipolar stimulation. In other embodiments, one or more electrodes (e.g., return electrodes) can be positioned remote from the target neural population for unipolar stimulation. Suitable techniques associated with the implantation procedure are known to practitioners skilled in the relevant art. After the signal deliver device 120 has been implanted in the patient P, a pulse system generates electrical pulses that are transmitted to the target neural population 104 by the first and second electrodes 121.

FIGS. 9A-12B illustrate signal delivery devices configured in accordance with a variety of embodiments for providing electromagnetic signals to patients suffering from ASD and/or other dysfunctions. Accordingly, these devices are representative of devices for performing the therapies described above. The illustrated devices include cranial implants that supply electrical current to the brain, as it is expected that such devices will provide direct treatment with relatively low power requirements. However, in other embodiments, other electromagnetic signals (e.g., magnetic fields) may be provided by other devices (e.g., transcranial magnetic stimulation devices).

Figure 9A:
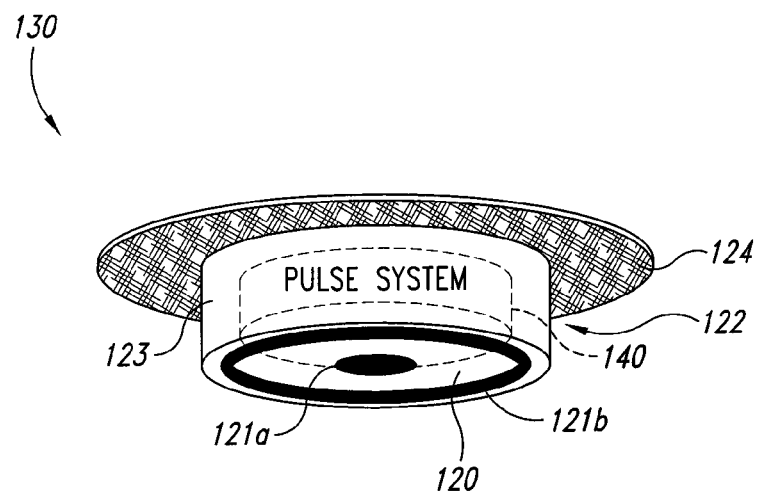
FIG. 9A is an isometric illustration of an implantable signal delivery device configured in accordance with an embodiment of the disclosure.

FIG. 9A is an isometric view of a system 130 configured in accordance with an embodiment of the disclosure for stimulating a region of the cortex proximate to the pial surface. The signal delivery system 130 can include an implantable signal delivery device 120 that in turn includes a support member 122, an integrated pulse system 140 (shown schematically) carried by the support member 122, and first and second electrodes 121 (identified individually by reference numbers 121a and 121b). The first and second electrodes 121 are electrically coupled to the pulse system 140. The support member 122 can be configured to be implanted into the skull or another intracranial region of a patient. In one embodiment, for example, the support member 122 includes a housing 123 and an attachment element 124 connected to the housing 123. The housing 123 can be a molded casing formed from a biocompatible material that has an interior cavity for carrying the pulse system 140. The housing 123 can alternatively be a biocompatible metal or another suitable material. The housing 123 can have a diameter of approximately 1-4 cm, and in many applications the housing 123 can be 1.5-2.5 cm in diameter. The housing 123 can also have other shapes (e.g., rectilinear, oval, elliptical) and/or other surface dimensions. The signal delivery system 130 can weigh 35 g or less and/or occupy a volume of 20 cc or less. The attachment element 124 can be a flexible cover, a rigid plate, a contoured cap, or another suitable element for holding the support member 122 relative to the skull or other body part of the patient. In one embodiment, the attachment element 124 is a mesh, such as a biocompatible polymeric mesh, metal mesh, or other suitable woven material. The attachment element 124 can alternatively be a flexible sheet of Mylar®, a polyester, or another suitable material.

Figure 9B:
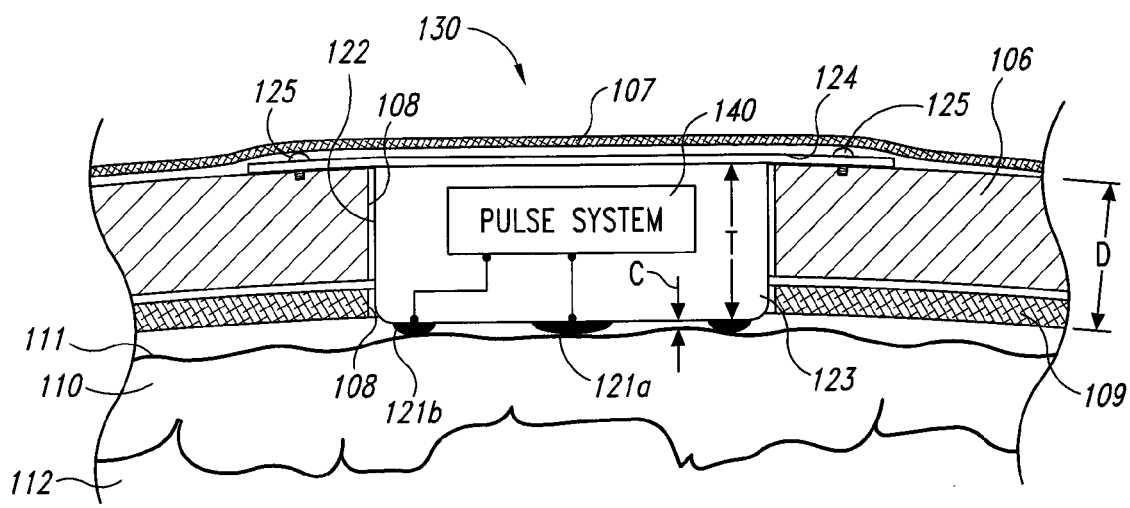
FIG. 9B is a cross-sectional view schematically illustrating an implantable signal delivery device configured in accordance with an embodiment of the disclosure.

FIG. 9B illustrates a cross-sectional view of the signal delivery system 130 after it has been implanted into a patient in accordance with an embodiment of the disclosure. In this particular embodiment, the system 130 is implanted into the patient by forming an opening in the scalp 107 and cutting a hole 108 through the skull 106 and through the dura mater 109. The hole 108 should be sized to receive the housing 123 of the support member 122, and in most applications, the hole 108 should be smaller than the attachment element 124. A practitioner inserts the support member 123 into the hole 108 and then secures the attachment element 124 to the skull 106. The attachment element 124 can be secured to the skull using a plurality of fasteners 125 (e.g., screws, spikes, etc.) or an adhesive. In another embodiment, a plurality of downwardly depending spikes can be formed integrally with the attachment element 124 to define anchors that can be driven into the skull 106.

The embodiment of the system 130 shown in FIG. 9B is configured to be implanted into a patient so that the electrodes 121 (e.g., electrodes 121a, 121b) contact a desired portion of the brain at the stimulation site. The housing 123 and the electrodes 121 can project from the attachment element 124 by a distance "D" such that the electrodes 121 are positioned at least proximate to the pia mater 111 surrounding the cortex 110. The electrodes 121 can project from the housing 123 as shown in FIG. 9B, or the electrodes 121 can be flush with the interior surface of the housing 123. In the particular embodiment shown in FIG. 9B, the housing 123 has a thickness "T" and the electrodes 121 project from the housing 123 by a distance "C" so that the electrodes 121 apply a given amount of pressure against the surface of the pia mater 111. The thickness of the housing 123 can be approximately 0.5-4 cm, and is more generally about 1-2 cm. The configuration of the signal delivery system 130 is not limited to the embodiment shown in FIGS. 9A-9B, but rather the housing 123, the attachment element 124, and the electrodes 121 can be configured to position the electrodes 121 in several different regions of the brain, and or in different manners. For example, in another embodiment, the housing 123 and the electrodes 121 can be configured to position the electrodes beneath the cortical surface (e.g., at a selected location from just below the cortical surface to deep within the cortex 110), and/or a deep brain region 112. Such techniques can be used to provide signals to cortical target neural populations within brain sulci and/or fissures, and/or beneath the cortical surface. In particular instances, stimulating deep brain structures may facilitate plasticity in ASD patients.

The pulse system 140 shown in FIGS. 9A-9B generates and/or transmits electrical pulses to the electrodes 121 to create an electrical field at the target neural population. The particular embodiment of the pulse system 140 shown in FIG. 9B is an "integrated" unit in that it is carried by the support member 122. The pulse system 140, for example, can be housed within the housing 123 so that the electrodes 121 can be connected directly to the pulse system 140 without having leads outside of the signal delivery device 120. The distance between the electrodes 121 and the pulse system 140 can be less than 4 cm, and it is generally 0.10 to 2.0 cm. The system 130 can accordingly provide electrical pulses to the target neural population without having to surgically create tunnels running through the patient to connect the electrodes 121 to a pulse generator implanted remotely from the signal delivery device 120. It will be appreciated, however, that in other embodiments, the pulse system 140 can be implanted separately from the signal delivery device 120, within or outside the cranium.

Figure 10:
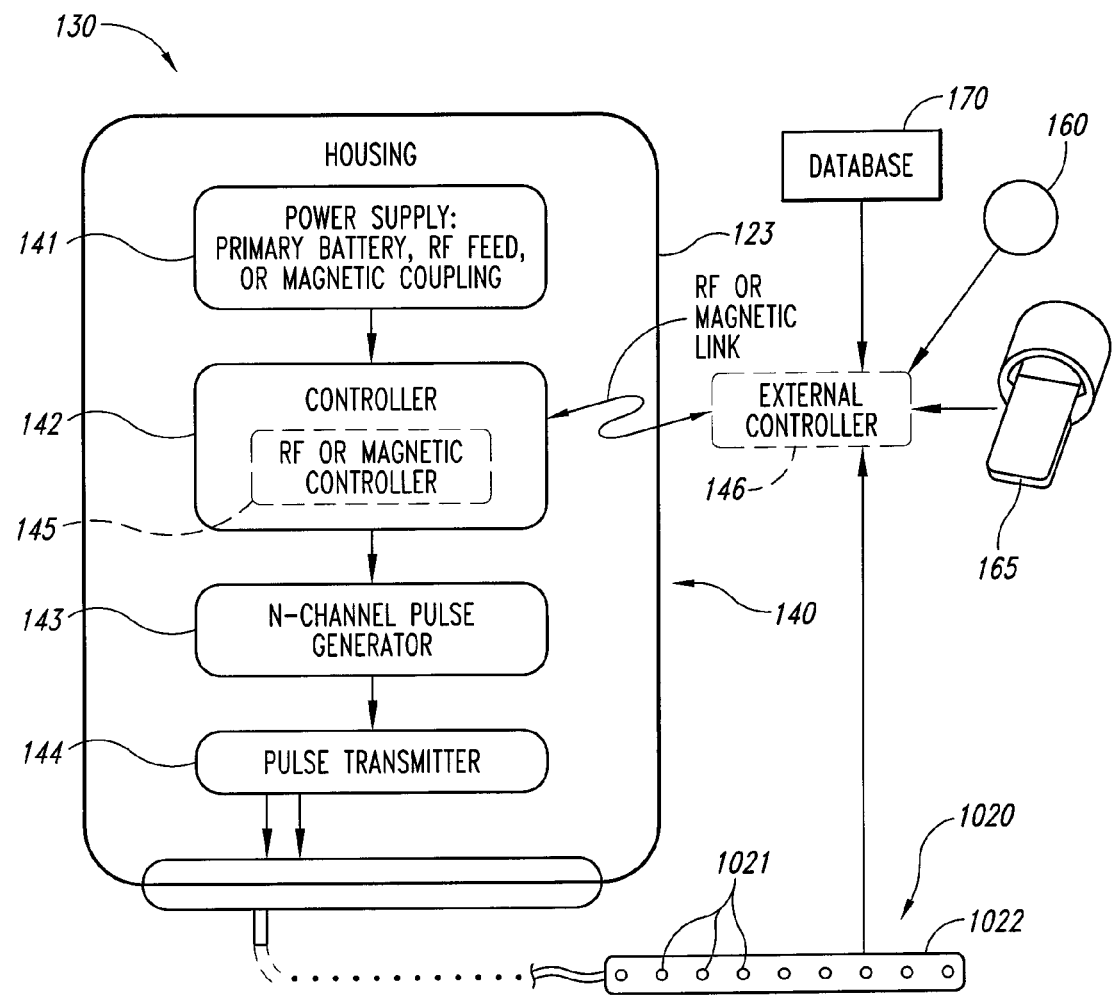
FIG. 10 illustrates a system for providing therapy to a patient in accordance with an embodiment of the disclosure.

FIG. 10 schematically illustrates details of an embodiment of the pulse system 140 described above. The pulse system 140 is generally contained in the housing 123, which can also carry a power supply 141, an integrated controller 142, a pulse generator 143, and a pulse transmitter 144. In certain embodiments, a portion of the housing 123 may comprise a signal return electrode. The power supply 141 can comprise a primary battery, such as a rechargeable battery, or other suitable device for storing electrical energy (e.g., a capacitor or supercapacitor). In other embodiments, the power supply 141 can be an RF transducer or a magnetic transducer that receives broadcast energy emitted from an external power source and that converts the broadcast energy into power for the electrical components of the pulse system 140.

In one embodiment, the integrated controller 142 can include a processor, a memory, and/or a programmable computer medium. The integrated controller 142, for example, can be a microcomputer, and the programmable computer medium can include software loaded into the memory of the computer, and/or hardware that performs the requisite control functions. In another embodiment identified by dashed lines in FIG. 10, the integrated controller 142 can include an integrated RF or magnetic controller 145 that communicates with the external controller 146 via an RF or magnetic link. In such an embodiment, many of the functions performed by the integrated controller 142 may be resident on the external controller 146 and the integrated portion 145 of the integrated controller 142 may include a wireless communication system.

The integrated controller 142 is operatively coupled to, and provides control signals to, the pulse generator 143, which may include a plurality of channels that send appropriate electrical pulses to the pulse transmitter 144. The pulse transmitter 144 is coupled to electrodes 1021 carried by a signal delivery device 1020. In one embodiment, each of these electrodes 1021 is configured to be physically connected to a separate lead, allowing each electrode 1021 to communicate with the pulse generator 143 via a dedicated channel. Accordingly, the pulse generator 143 may have multiple channels, with at least one channel associated with each of the electrodes 1021. Suitable components for the power supply 141, the integrated controller 142, the external controller 146, the pulse generator 143, and the pulse transmitter 144 are known to persons skilled in the art of implantable medical devices.

The pulse system 140 can be programmed and operated to adjust a wide variety of stimulation parameters, for example, which electrodes 1021 are active and inactive, whether electrical stimulation is provided in a unipolar or bipolar manner, and/or how stimulation signals are varied. In particular embodiments, the pulse system 140 can be used to control the polarity, frequency, duty cycle, amplitude, and/or spatial and/or topographical qualities of the stimulation. The stimulation can be varied to match, approximate, or simulate naturally occurring burst patterns (e.g., theta-burst and/or other types of burst stimulation), and/or the stimulation can be varied in a predetermined, pseudorandom, and/or other aperiodic manner at one or more times and/or locations. The signals can be delivered automatically, once initiated by a practitioner. The practitioner (and, optionally, the patient) can override the automated signal delivery to adjust, start, and/or stop signal delivery on demand.

In particular embodiments, the pulse system 140 can receive information from selected sources, with the information being provided to influence the time and/or manner by which the signal delivery parameters are varied. For example, the pulse system 140 can communicate with a database 170 that includes information corresponding to reference or target parameter values. The database 170 can be updated as the patient undergoes therapy, e.g., via the evaluation/adjunctive therapy system 135 described above with reference to FIG. 1B. Sensors 160 can be coupled to the patient to provide measured or actual values corresponding to one or more parameters. The sensors 160 can be coupled to the patient's central nervous system (e.g., to the patient's motor cortex) to detect brain activity corresponding to incipient and/or actual hypertonicity behaviors. In particular embodiments, the sensors 160 can include ECoG or EEG sensors. In another embodiment, the sensors 160 can be peripheral sensors. In any of these embodiments, the measured values of the parameter can be compared with the target value of the same parameter (e.g., performance of a particular task), and the pulse system 140 can be activated if the measured value differs from the target value by more than a threshold amount. Accordingly, this arrangement can be used in a closed-loop fashion to control when stimulation is provided and when stimulation may cease. In one embodiment, some electrodes 1021 may deliver electromagnetic signals to the patient while others are used to sense the activity level of a neural population. In other embodiments, the same electrodes 1021 can alternate between sensing activity levels and delivering electrical signals. In either of these particular embodiments, information received from the signal delivery device 1020 can be used to determine the effectiveness of a given set of signal parameters and, based upon this information, can be used to update the signal delivery parameters and/or halt the delivery of the signals.

In other embodiments, other techniques can be used to provide patient-specific feedback. For example, a magnetic resonance chamber 165 can provide information corresponding to the locations at which a particular type of brain activity is occurring and/or the level of functioning at these locations, and can be used to identify additional locations and/or additional parameters in accordance with which electrical signals can be provided to further increase and/or facilitate functionality. Accordingly, the system can include a direction component configured to direct a change in an electromagnetic signal applied to the patient's brain based at least in part on an indication received from one or more sources. These sources can include a detection component (e.g., the signal delivery device and/or the magnetic resonance chamber 165).

Figure 11:
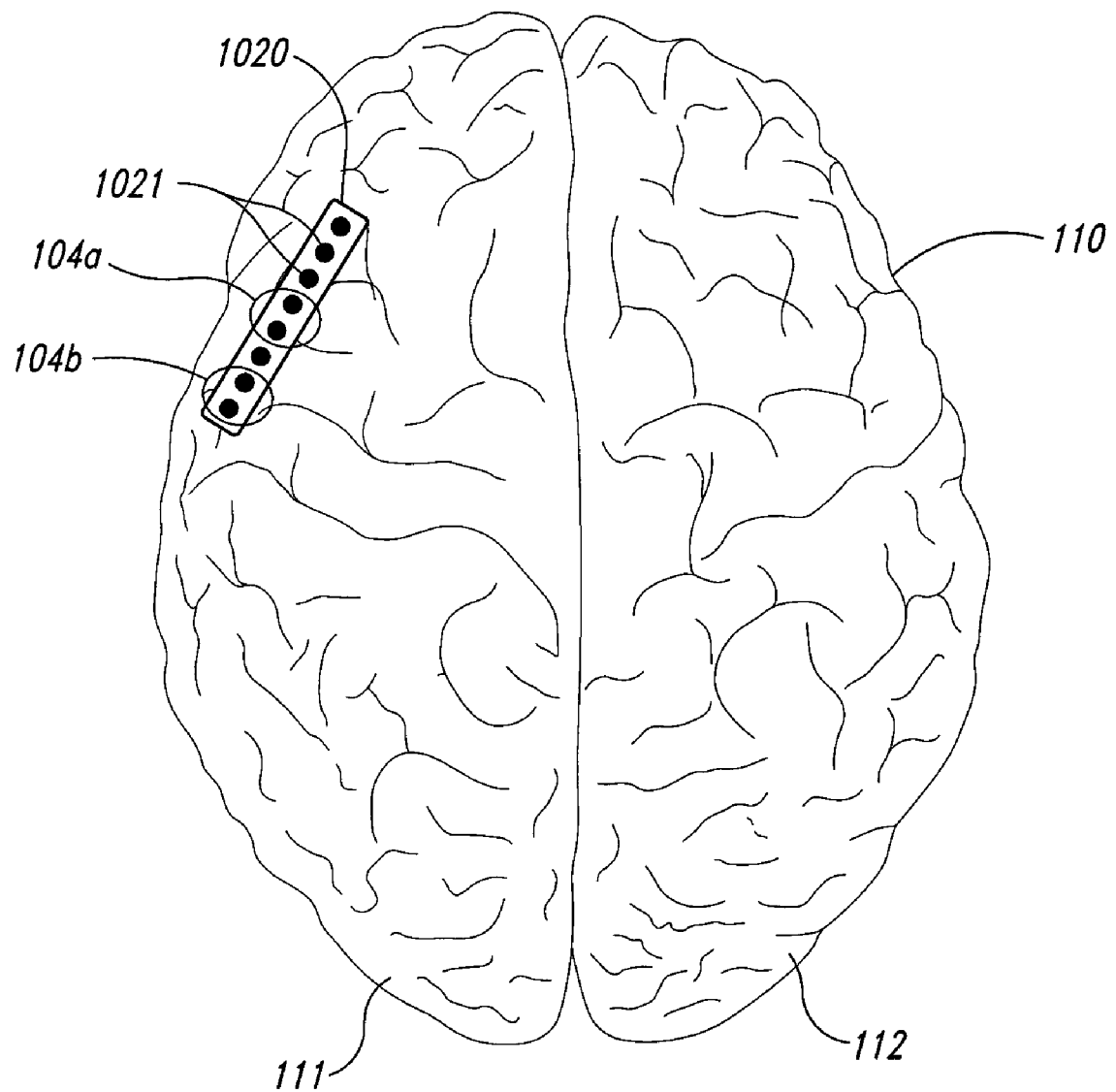
FIG. 11 is a top plan view of a portion of the brain with a signal delivery device positioned in accordance with a particular embodiment of the disclosure.

One aspect of the signal delivery device 1020 shown in FIG. 10 is that it can include a support member 1022 that carries multiple electrodes 1021 spaced apart along the generally linear axis. This arrangement can be used to provide electrical signals to multiple target neural populations, and/or to determine a particularly efficacious target neural population by trial and error. FIG. 11 illustrates the signal delivery device 1020 positioned over the left hemisphere 111 of the patient's brain 110, so as to provide some electrodes 1021 over a first target neural population 104a (e.g., the superior temporal sulcus and/or other target site(s) associated with neural processing), and others over the second neural target neural population 104b (e.g., the superior temporal gyrus and/or other target site(s) associated with auditory processing). Accordingly, the same signal delivery device 1020 can apply signals to multiple sites, with power to each of the electrodes 1021 controlled individually so as to provide signals to the appropriate site at the appropriate time and in accordance with the appropriate signal delivery parameters. In an analogous manner, one or more electrodes may be positioned proximate to target neural populations at the patient's right hemisphere 112.

Figure 12A:
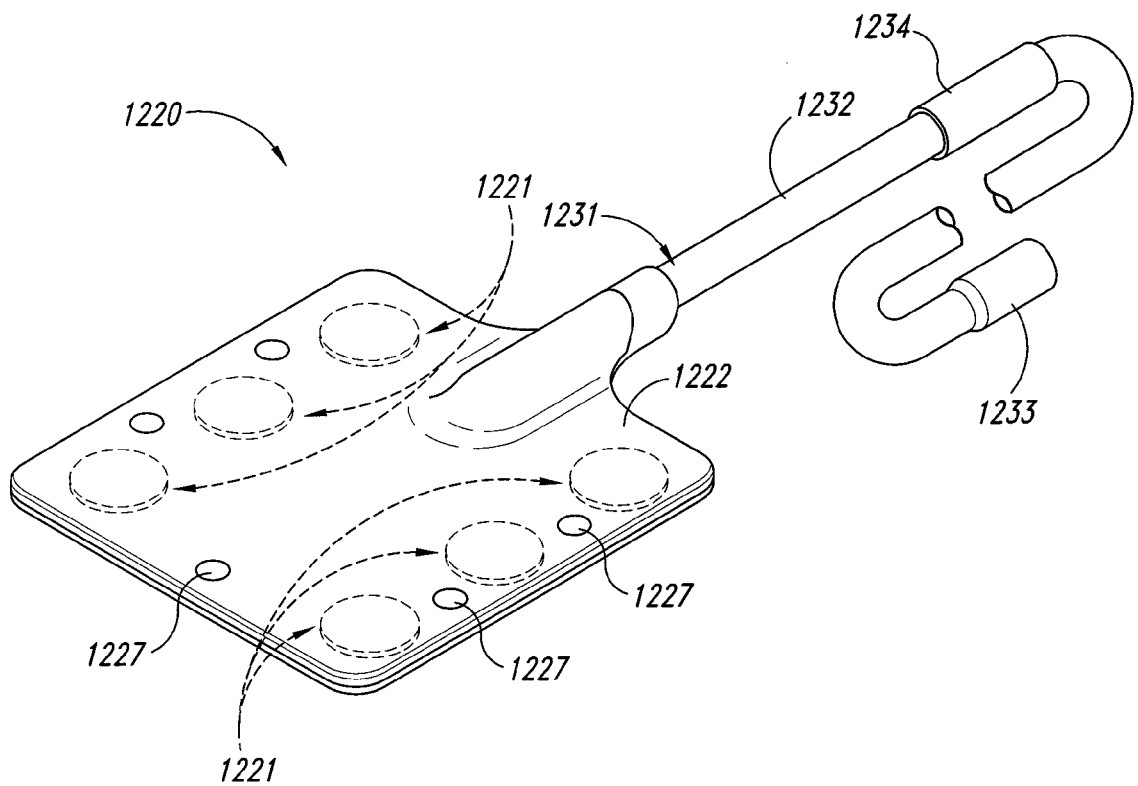
FIG. 12A is a top, partially hidden isometric view of a signal delivery device configured in accordance with another embodiment of the disclosure.

In other embodiments, the system can include signal delivery devices having other configurations. For example, FIG. 12A is a top, partially hidden isometric view of a signal delivery device 1220, configured to carry multiple cortical electrodes 1221 in accordance with another embodiment. The electrodes 1221 can be carried by a flexible support member 1222 to place each electrode 1221 in contact with a target neural population of the patient when the support member 1222 is implanted. Electrical signals can be transmitted to the electrodes 1222 via leads carried in a communication link 1231. The communication link 1231 can include a cable 1232 that is connected to the pulse system 140 (FIG. 10) via a connector 1233, and is protected with a protective sleeve 1234. Coupling apertures or holes 1227 can facilitate temporary attachment of the signal delivery device 1220 to the dura mater at, or at least proximate to, a target neural population. The electrodes 1221 can be biased cathodally and/or anodally. In an embodiment shown in FIG. 12, the signal delivery device 1220 can include six electrodes 1221 arranged in a 2×3 electrode array (i.e., two rows of three electrodes each, with rows spaced from each other by about 18 mm, and electrodes 1221 within the row spaced by about 9 mm), and in other embodiments, the signal delivery device 1220 can include more or fewer electrodes 1221 arranged in symmetrical or asymmetrical arrays. The particular arrangement of the electrodes 121 can be selected based on the region of the patient's brain that is to be stimulated, and/or the patient's condition.

Figure 12B:
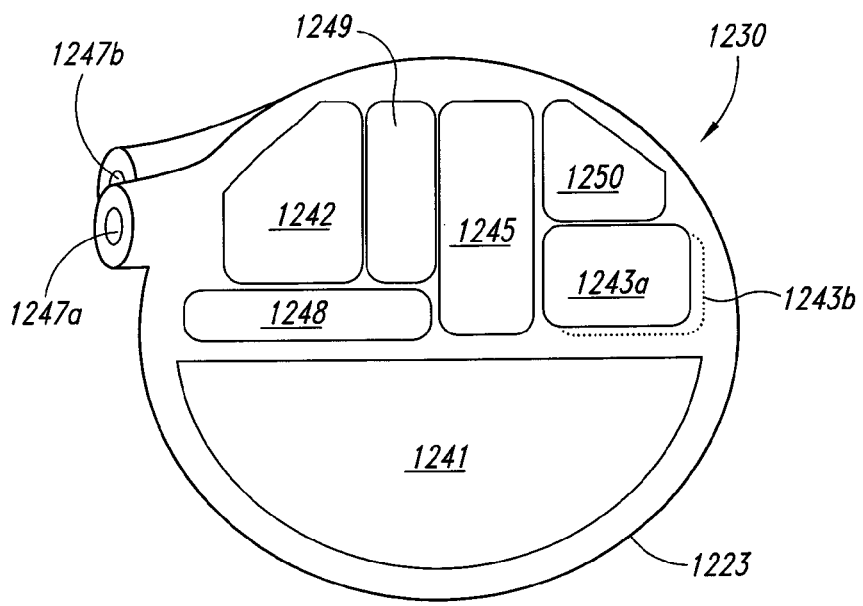
FIG. 12B is an internal block diagram of a signal delivery device configured in accordance with yet another embodiment of the disclosure.

FIG. 12B is an internal block diagram of a system 1230 configured in accordance with another embodiment of the invention. The system 1230 can include multiple pulse generators 1243a, 1243b and multiple outputs 1247a, 1247b. Accordingly, the system 1230 may be coupled to two or more signal delivery devices (e.g., two of the devices 1220 shown in FIG. 12A) to apply electromagnetic signals to different target neural populations in one or more manners, which may depend upon the nature or extent of a patient's neurologic dysfunction and/or other embodiment details. The different target neural populations may reside in a variety of anatomical locations, as discussed above. For example, a first and a second target neural population may reside in the same or different brain hemispheres. A system having multiple pulse generators 1243a, 1243b may stimulate different neural populations simultaneously or separately, in an independent or correlated manner. One or both pulse generators 1243a, 1243b may generate stimulation signals in various manners described herein.

Other features of the system 1230 include a hermetically sealed housing 1223 that houses a power source 1241 as well as a controller 1242, a telemetry and/or communication unit 1245, and a switching unit 1250. Depending upon embodiment details, the system 1230 may further comprise at least one programmable computer medium (PCM) 1248, which may be coupled to the controller 1242, the telemetry/communication unit 1245, the pulse generators 1243a, 1243b, and/or the switching unit 1250. The system 1230 may additionally comprise at least one timing unit 1249.

The power source 1241 can include a charge storage device such as a battery. In some embodiments, the power source 1241 may additionally or alternatively comprise another type of device for storing charge or energy, such as a capacitor. The controller 1242, the PCM 1248, the telemetry/communication unit 1245, the pulse generators 1243a, 1243b, the switching unit 1250, and/or the timing unit 1249 may include integrated circuits and/or microelectronic devices that synergistically produce and manage the generation, output, and/or delivery of stimulation signals. In certain embodiments, one or more elements within the system 1230 (e.g., the communication unit 1245, the pulse generators 1243a, 1243b, the switching unit 1250, and/or other elements) may be implemented using an Application Specific Integrated Circuit (ASIC).

The timing unit 1249 may include a clock or oscillator and/or circuitry associated therewith configured to generate or provide a set of timing reference signals to the controller 1242, the PCM 1248, the telemetry/communication unit 1245, the pulse generators 1243a, 1243b, the switching unit 1250, and/or one or more portions, subelements, or subcircuits of the system 1230. Such elements, subelements, and/or subcircuits may correlate or synchronize one or more operations to one or more timing reference signals, including the generation of other signals in a manner understood by those skilled in the art.

The controller 1242 may control, manage, and/or direct the operation of elements within the system 1230, e.g., on a continuous, near-continuous, periodic, or intermittent basis depending upon embodiment details. The controller 1242 may include one or more portions of an integrated circuit such as a processing unit or microprocessor, and may be coupled to the programmable computer medium (PCM) 1248. The PCM 1248 may comprise one or more types of memory including volatile and/or nonvolatile memory, and/or one or more data or signal storage elements or devices. The PCM 1248 may store an operating system, program instructions, and/or data. The PCM 1248 may store treatment program information, system configuration information, and stimulation parameter information that specifies or indicates one or more manners of generating and/or delivering stimulation signals in accordance with particular embodiments of the invention.

The switching unit 1250 can include a switch matrix and/or a set of signal routing or switching elements that facilitate the application, delivery, and/or routing of stimulation signals to one or more sets of electrode assemblies, electrical contacts, and/or signal transfer devices at any given time. In one embodiment, the switching unit 1250 may facilitate the electrical activation of particular electrode assemblies, contacts, and/or signal transfer devices, possibly while other such elements remain electrically inactive or electrically float.

Representative Diagnostic Procedures and Adjunctive Therapies

The following discussion provides additional details regarding procedures for diagnosing ASD, and for supplementing the electromagnetic signal delivery treatment described above. In many instances, at least some aspects of the diagnostic procedure can also be used as part of an adjunctive therapy regimen, e.g., a behavioral therapy regimen that is performed in conjunction with electromagnetic stimulation to enhance neural connections and/or otherwise facilitate use of the patient's natural neuroplasticity to address ASD.

In general, a representative procedure for treating ASD can take the following form. First, using DSM IV and/or other assessments, a child with pervasive developmental disorders (e.g., ASD), is evaluated to find specific and prominent deficits that characterize the symptomology. Second, an assay is designed to determine the process or processes underlying the deficit. The procedure generally includes a test assessment, data collection and theoretical analysis for each child individually. The outcome determines, at least in part, the nature of the adjunctive therapy and the location(s) of the corresponding electromagnetic signal delivery sites and associated signal delivery parameters. Four representative implementations in social and communicative contexts are described below.

Example: Social Interaction

Diagnosis. In this example, a child is assessed as positive on the characteristics of DSM IV 1. The child exhibits qualitative impairment in social interactions, as manifested by at least two of the following: marked impairment in the use of multiple nonverbal behaviors such as eye-to-eye gaze, facial expression, body postures, and gestures to regulate social interaction. A representative assessment is expected to identify (e.g., pinpoint) the deficit as being associated with either or both of two independent processes: hypo- or hypersensitivity of the nonverbal inputs corresponding to the nonverbal behaviors, and/or the inappropriate sensory integration of the inputs corresponding to the nonverbal behaviors.

Recognizing Emotion. An important feature of social interactions is for participants to be cognizant of the ongoing emotions of other participants in the encounter. Important signals of emotion are available from two sources: the face (e.g., visual signals), and the voice (e.g., auditory signals). Using these signals involves analyzing the information in each signal and integrating (e.g., appropriately combining) the two signals to understand the emotion. Using the test and theoretical paradigm described further below, the facial and vocal information presented to the patient is manipulated to determine (a) if the patient is sensitive to these independent signals and (b) if they are integrated appropriately.

Figures 13, 14:
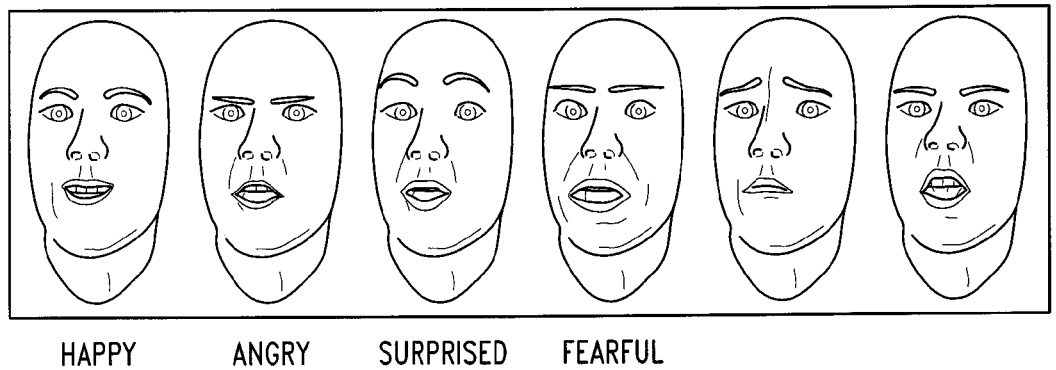
FIG. 13 illustrates a computer-generated image of a human head and face displaying each of six facial emotions during the articulation of the word "please."
FIG. 14 illustrates an expanded factorial design for four auditory emotion categories and four visual emotion categories.

FIG. 13 illustrates a synthetic talking head, Baldig, programmed to express each of six emotional states during the articulation of a test word. The test word can be a semantically neutral stimulus word (e.g., "please") that is presented in any of the different simulated emotional states. In a particular embodiment, four of the six emotion categories (happy, angry, surprised, and fearful) are used to assess the patient. In this embodiment, the emotional expression presented by the face, and the emotion conveyed by the articulation of the test word can be varied in a dependent manner to produce visually and auditorily consistent stimuli, or the facial expression and voice can be varied independently of each other to produce inconsistent stimuli. Further details regarding the Baldie software are provided at www.animatedspeech.com and www-.mamboucsc.edu/psd/dwm.

Using an expanded factorial design shown in FIG. 14, the four emotions (happy, angry, surprised, and fearful) are presented auditorily, visually, and bimodally for a total of 24 combinations. For the eight unimodal presentations, either just the face or just the voice is presented. For the sixteen bimodal presentations, the synthetic face is presented along with the synthetic voice. Each audible word is presented with each visible word for a total of sixteen unique conditions. Twelve of the sixteen bimodal words have inconsistent auditory and visual information. In a particular embodiment, all of these conditions are used to achieve an informative picture of how these two modalities are processed.

Establishing a Standard. To implement this procedure with autistic individuals, the practitioner will typically want to compare individual patient data with data obtained from normal subjects. Accordingly, the paradigm can be carried out with normally developing individuals to obtain normative results at several age levels. To establish the standard, normally developing children are instructed to watch the talking head and listen to the voice during each trial. The children are then asked to indicate which of the four emotion categories is being communicated. The children can make their responses by entry into a computer (e.g., via the input devices 102 shown in FIG. 1B) or by other suitable methodologies. All of the test conditions can be randomized and presented repeatedly for identification. The mean observed proportion of identifications can be computed for each of the 24 conditions for each child. Two groups of 24 students each can be tested to give a standard for two age groups, e.g., five year olds and adolescents. In other embodiments, standards for other age groups and/or more specific age groups can be established.

Figure 15:
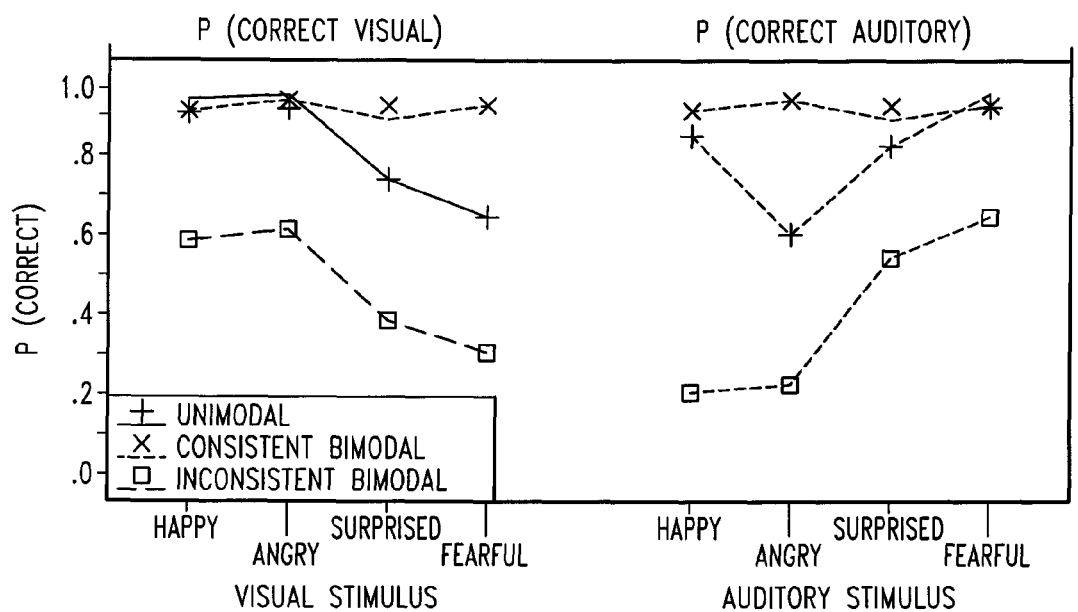
FIG. 15 illustrates the probability of correct responses from a hypothetical control group of normal adolescent subjects as a function of visual and auditory stimuli corresponding to four different emotional categories.

FIG. 15 illustrates results from a hypothetical control group of adolescents. Given that the participants' goal is to perceive the emotion, it is informative to evaluate performance in terms of accuracy with respect to each of the two modalities. The points in the left half of FIG. 15 show average performance scored in terms of accuracy with respect to the visible emotion. For unimodal trials, the average correct performance, given just the face, is 0.94, 0.95, 0.73, and 0.64 for the emotion categories of happy, angry, surprised, and fearful, respectively. Thus, the average, normal subject is fairly good at identifying the correct emotion from just the face, even when viewing a synthetic head.

The right half of FIG. 15 illustrates performance scored in terms of accuracy with respect to the auditory emotion. On the basis of unimodal trials, correct identification given just the auditory information averaged 0.85, 0.60, 0.82, and 0.96 for the auditory emotion categories of happy, angry, surprised, and fearful, respectively. For the average, normal subject, happy, surprised, and fearful were relatively easy to identify in the voice, whereas angry was somewhat more difficult.

There is evidence that recognizing auditory speech and facial information improves across development (see, for example, Massaro, 1987, Chapter 8; and Massaro, D. W. (1998) "Perceiving talking faces: from speech perception to a behavioral principle"; Cambridge, Mass.: MJT Press (hereinafter, "Massaro, 1998") at 141-143). Therefore, it is expected that data for average, normal 5 year olds will be about half as accurate as for the adolescents shown in FIG. 15.

Patient Evaluation. Given the foregoing standard, autistic patients can be tested and evaluated appropriately against the standard. The patients are instructed to watch the talking head and listen to the voice during each trial, and to indicate which of the four emotion categories is being communicated. The patients can make their responses by inputs to a computer (or via another suitable technique) using a patient-appropriate response method. Noninformative rewards or inducements can be presented to keep each patient involved in the assessment. The test conditions can be randomized and presented repeatedly for identification. The mean observed proportion of identifications can be computed for each of the 24 conditions for each patient.

The results for autistic patients can then be compared to results for normal subjects. In a representative example, the average correct performance of an autistic patient for unimodal trials, given just the face, may be 0.65, 0.55, 0.44, and 0.33 for the emotion categories happy, angry, surprised, and fearful, respectively. These performance values are significantly poorer than performance values for the adolescent standard group (0.94, 0.95, 0.73, and 0.64, respectively, as shown in FIG. 15). Thus, this patient reveals a significant deficit in recognizing emotion from the face. Given this outcome, the practitioner can select an adjunctive treatment that includes a training program directed to improving the patient's ability to recognize expressions of facial emotion. In addition, this information can be used by the practitioner to bracket and/or pinpoint brain area(s) suitable for electromagnetic stimulation.

Figures 16A, 16B, 16C:
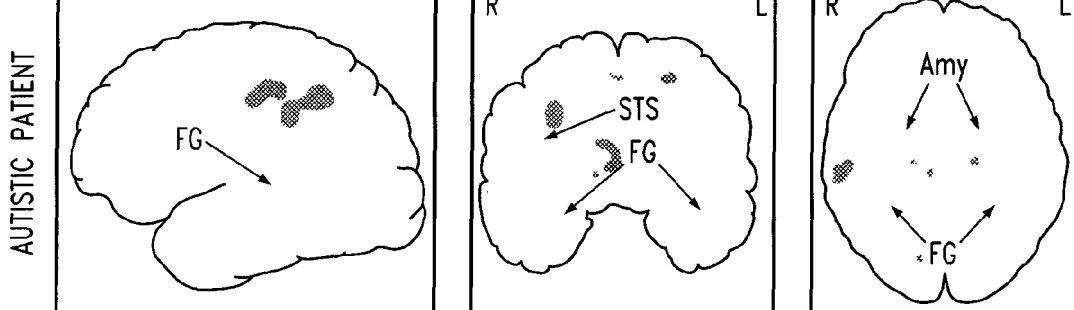
FIGS. 16A-16F illustrate representative active brain regions for normal subjects and autistic subjects responding to emotions presented by a face.
Figures 16D, 16E, 16F:
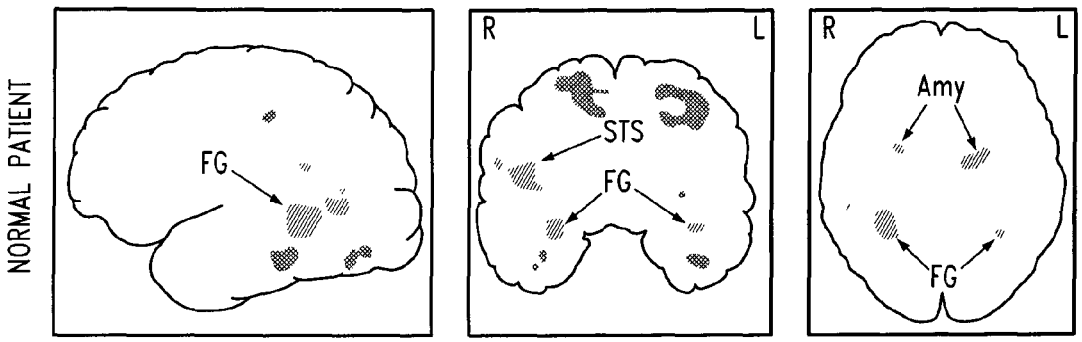

A representative adjunctive treatment can include a behavioral therapy using, for example, the Baldi® software described in this disclosure, or a therapist trained in techniques designed to develop the ability to recognize facial emotions. The adjunctive treatment can augment treatment via electrical and/or magnetic cortical stimulation. This stimulation can be targeted to specific cortical regions that normal subjects use to process visual information received by viewing faces, including the right Fusiform Face Area which is located on the fusiform gyrus (FG, Brodmann area 36) on the ventral surface of the temporal lobe. Existing studies have shown that this region is hypoactive in ASD patients as compared to normal subjects. For example, FIGS. 16A-16F (adapted from Piercek et al; Brain (2001) 124:2059-2073, hereinafter "Piercek, 2001"), illustrate this effect. FIGS. 16A-16C illustrate T maps for autistic patients, with areas indicating statistically significant de-activation identified by crosshatching on saggital, coronal, and axial cuts, respectively. FIGS. 16D-16F illustrate corresponding T maps for normal patients, with regions exhibiting statistically significant de-activation indicated by crosshatching, and regions indicating statistically significant positive activation indicated by hatching. By comparing FIGS. 16A-16C with corresponding FIGS. 16D-16F, it is evident that autistic patients have hypoactive neural populations at the FG, the right superior temporal sulcus (STS) and the left amygdala (Amy). Accordingly, the foregoing sites are representative of sites a practitioner may select for electromagnetic stimulation in a patient exhibiting deficits in the ability to recognize facial emotions.

Figure 17A:
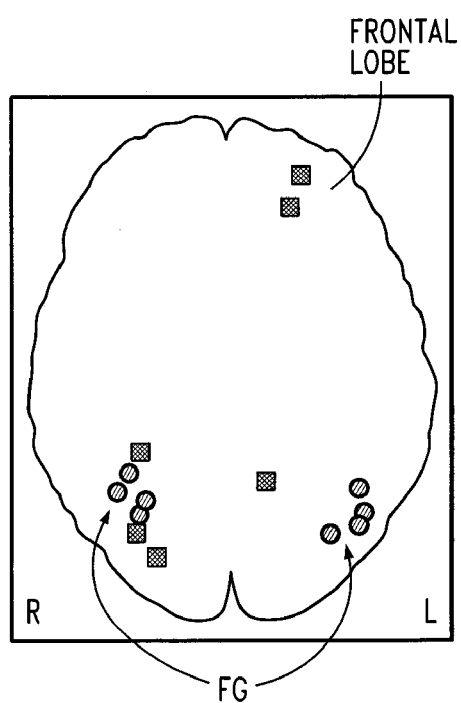
FIGS. 17A-17B further illustrate active brain regions for normal and autistic subjects when responding to emotions presented by a face.
Figure 17B:
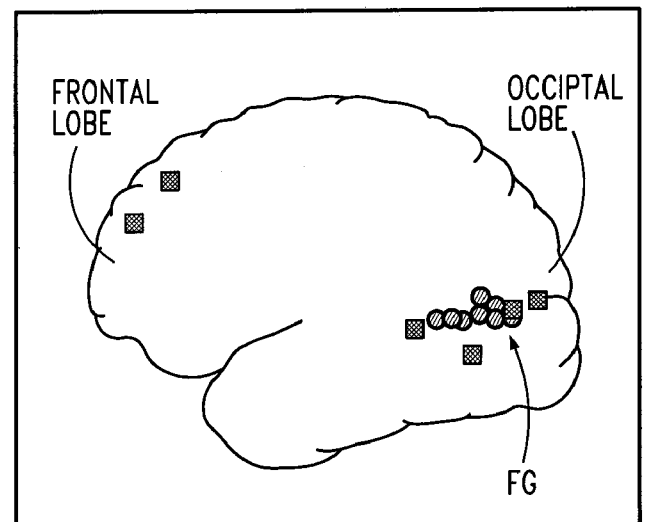

Results shown in FIG. 16A-16F are derived from group-averaged Talairach-normalized fMRI images. Unlike the normal subjects, ASD patients do not exhibit a consistent location of significant activation in response to faces. Examination of individual-specific sites of maximal activation in ASD patients reveals a distinct region of functional activation that can vary on a patient-by-patient basis, as shown in FIGS. 17A-17B (adapted from Piercek, 2001). FIG. 17A illustrates a composite axial view of the brain, and FIG. 17B illustrates a composite saggital view of the brain. Each symbol shown in FIGS. 17A and 17B represents an activation "hot spot" for a single subject. For purposes of illustration, peak activations are shown collapsed across the superior-to-inferior axis on the axial image (FIG. 17A) and across the left-to-right axis on the saggital image (FIG. 17B). Peak activations are shown with squares for autistic patients, and with circles for normal patients. For every normal subject in this study, the site of maximum activity was located in the FG. By contrast, each ASD patient displayed a unique hot spot, only some of which were located in the FG, while other were located in the frontal lobe, occipital lobe, and cerebellum. Variability in the location of maximal functional activation, and/or the level of activation in the FG, is expected to account for the behavioral deficit that ASD patients experience in reading emotions from faces, and is expected to contribute to their social impairments. Behavioral training coupled with cortical stimulation in one or more of the regions shown to be involved in emotional face processing is expected to produce an increase in functional activation in these regions, and lead to behavioral improvements in ASD patients.

FIGS. 18A-18F (based on information presented in Piercek, 2001) further illustrate representative target neural populations in accordance with particular embodiments. FIG. 18A is a ventral view of the brain illustrating the middle temporal gyrus (mTG), the inferior temporal gyrus (iTG) and the fusiform gyrus (FG). FIG. 18B is a coronal section of the brain, and FIG. 18C is a detailed portion of the coronal section shown in FIG. 18B, with the middle temporal gyrus, inferior temporal gyrus, and fusiform gyrus highlighted. FIG. 18D is a left lateral view of the brain with the amygdala (Amy) highlighted. FIG. 18E is a coronal section of the brain, also highlighting the amygdala, and FIG. 18F is a detailed view of a portion of the coronal section shown in FIG. 18E.

During a representative treatment regimen, the patient is instructed (e.g., via text presented at a computer display, such as the output device 105 shown in FIG. 1B) to watch Baldi and indicate which emotion was shown in the face. A 200 ms beep sounds prior to the presentation of the test stimulus to indicate the start of each trial. Following the test presentation, response buttons appear in the upper left hand corner of the display. The patient can respond by activating a corresponding soft button labeled "happy," "angry," "surprised," or "fearful" using the mouse, keypad, or touch screen. After the patient's response, the process can include providing feedback (e.g., via the display, or by the practitioner) indicating the correct emotion that was presented. The emotion stimulus is then repeated along with a description of the emotion. To keep the patient engaged, additional feedback can be given for correct responses in the form of "stickers" and verbal praise given by Baldi. Training can continue at least until the child's performance shows the normal skill in recognizing emotion in the face. Some overtraining may also be called for to achieve good retention.

Figure 19A:
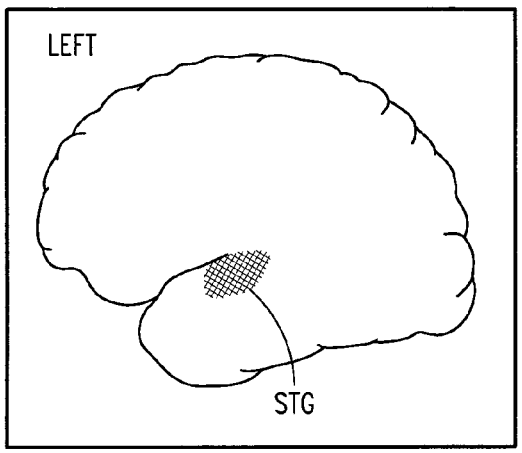
FIGS. 19A-19B illustrate representative hypoactive areas in autistic patients.
Figure 19B:
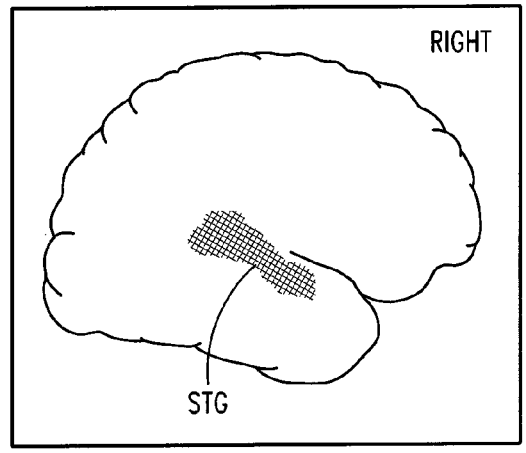

A generally similar evaluation (and, when indicated, a corresponding treatment regimen) can be carried out in the context of auditory emotions. Returning to FIG. 15, a hypothetical standard for a normal adolescent subject is shown on the right side of FIG. 15. On the basis of unimodal trials, normal subjects presented with just the auditory information (e.g., just a voice saying "please") averaged 0.85, 0.60, 0.82, and 0.96 for the auditory emotion categories happy, angry, surprised, and fearful, respectively. As indicated by these scores, happy, surprised, and fearful emotional states are relatively easy to identify in the voice, whereas anger is somewhat more difficult. If an individual patient performs significantly poorer than these standard values, the patient can receive a treatment that includes facial emotion training to train the patient to recognize emotions from speech. In particular, the training treatment can include a behavioral therapy using, for example, the Baldi® software as described in this disclosure, or a therapist trained in techniques designed to develop the ability to recognize emotions from speech, in combination with electrical or magnetic cortical stimulation. This stimulation can be targeted at specific cortical regions including the superior temporal gyrus (STG), and especially the right STG, (Brodmann areas 22 and 42), as shown in FIGS. 19A and 19B, which are based on information presented by M. Zilbovicius et al. (2000) in Am. J. Psychiatry (157:1988-1993).

If the patient is reasonably capable of recognizing emotion in the face and voice, the practitioner can assess the patient's multimodal integration capabilities. FIG. 15 provides a representative standard for normal adolescents performing multimodal integration tasks. Accuracy data are presented in FIG. 15 for bimodal trials, separately according to whether the two modalities are consistent or inconsistent with one another. Consistent modalities refer to multiple modalities simultaneously corresponding to the same emotion (e.g., both facial expression and voice exhibiting a happy emotion) and inconsistent modalities refer to multiple modalities simultaneously corresponding to different emotions (e.g., a happy facial expression coupled with an angry voice). When measured relative to the unimodal results, the bimodal results show a large influence of both modalities on performance. Bimodal performance is expected to be close to perfect for all four emotion categories when the modalities are consistent. Thus, overall performance is more accurate with two sources of consistent information than with either source of information alone. Conversely, given inconsistent information from the two sources, performance is poorer than observed in the unimodal conditions. The disruptive effect of inconsistent sources held strongly for all four emotion categories, with performance being poorer than observed when unimodal information was presented to the subject.

Figure 20:
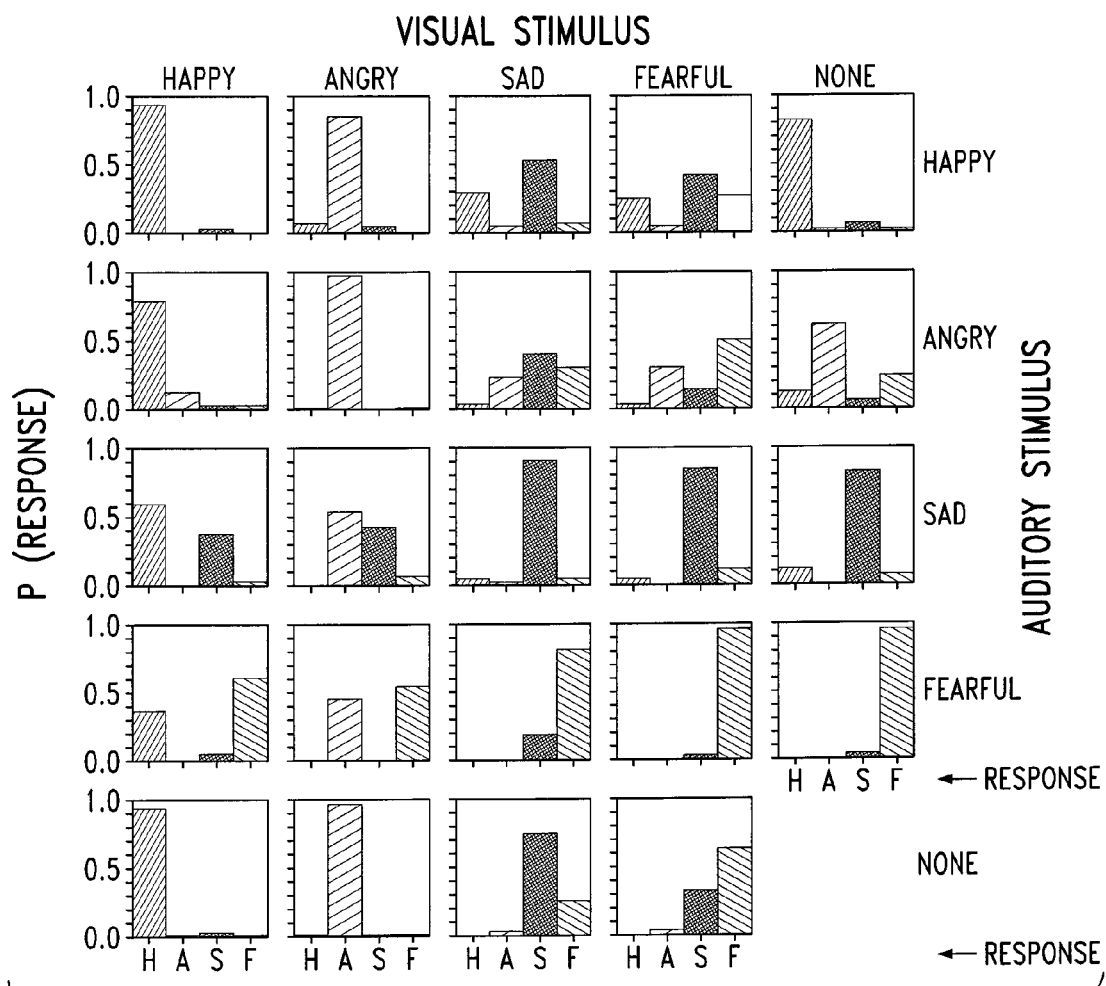
FIG. 20 illustrates the proportion of correct responses by representative normal subjects when presented with unimodal and bimodal auditory and visual stimuli corresponding to four different emotional categories in accordance with a particular embodiment.

FIG. 20 illustrates the fraction of times each stimulus event was identified as a particular emotion, for each combination of visual and auditory stimuli. For example, the left-most box in the top row of FIG. 20 indicates that when normal subjects are presented with a happy face and a happy voice, nearly all the subjects identify the emotion as happy. The next box to the right in the top row of FIG. 20 indicates that when normal subjects are presented with an angry face and a happy voice, nearly all identify the emotion as anger, but some identify the emotion as happiness, and others as sadness. Although the results in FIGS. 15 and 20 demonstrate that both the face and the voice are used in emotion perception, they do not indicate that they were necessarily integrated. A formal theoretical analysis of these fine-grained results can accordingly be used to determine whether the facial and vocal emotions were integrated appropriately.

The analysis results shown in FIG. 20 provide a measure of what alternatives are perceived given the different test conditions. Multimodal sensory integration predicts that perception will consist of the most reasonable alternative given the two inputs. This means that the two modalities are a better predictor of bimodal performance than just a single modality. The combination of surprise and fear provides an illustrative example. As can be seen in FIG. 20, when auditory surprise is paired with visual fear, surprise is the dominant judgment. On the other hand, when auditory surprise is paired with visual anger, anger is the dominant judgment. The difference between these two cases can be understood by the information available in the various inputs. In both cases, the dominant response is that which agrees with the least ambiguous source of information. Auditory surprise is less ambiguous than visual fear (see FIG. 15), hence when they are combined, surprise is the dominant judgment. Auditory surprise is more ambiguous than visual anger (see FIG. 15), hence when they are combined, anger is the dominant judgment. These results are qualitatively consistent with the principle that the influence of one source of information when combined with another source is related to the relative ambiguity of the sources when presented in isolation. The exact test of the influence of the two sources, and whether sensory integration occurs, involve model testing, which can be carried out on each patient. Additional details are provided in Massaro, 1998.

Figure 21A:
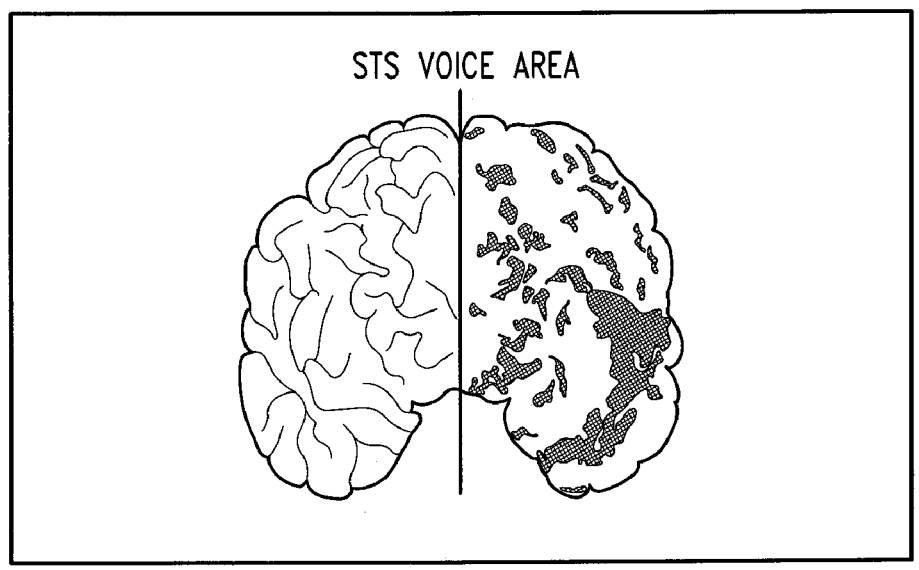
FIG. 21A illustrates representative brain areas active during speech processing in a normal subject, and FIG. 21B compares active brain areas for normal and autistic subjects.
Figure 21B:
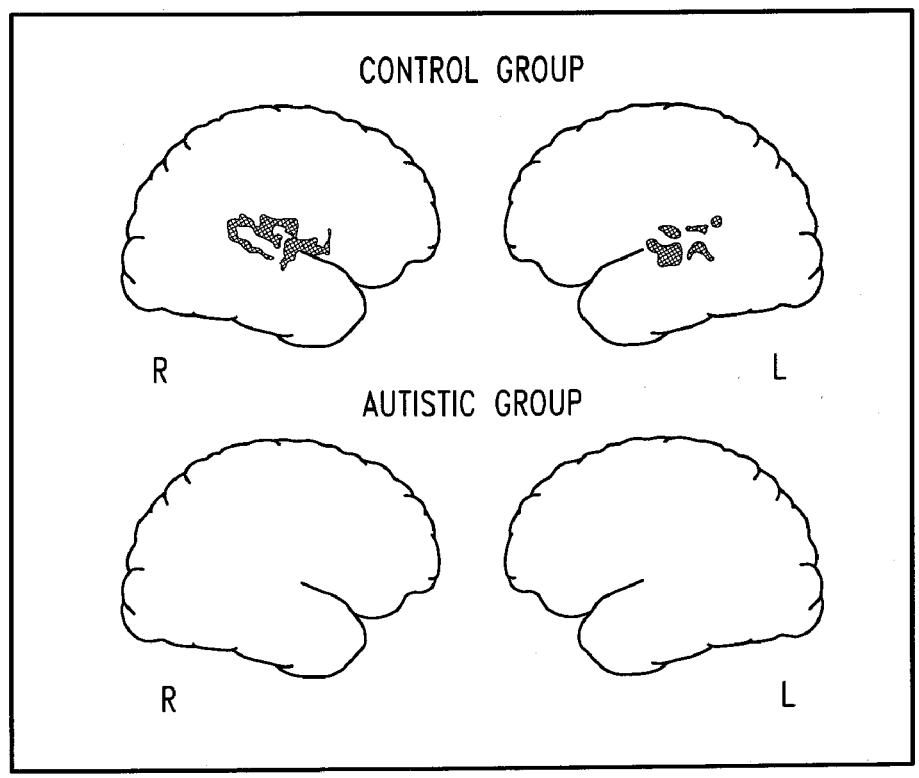

Once the practitioner has assessed the patient's ability to recognize emotion in the face and voice, the practitioner can assess the patient's ability to integrate the auditory and visual expressions of emotion. If, based on a comparison with the data shown in FIGS. 15 and 20, an individual patient exhibits a deficit in multimodal sensory integration, the patient can receive a treatment program that emphasizes integrating sensory information from visual and auditory to recognize emotions from facial expressions and speech. The treatment can include a behavioral therapy using, for example, the Baldi® software described above, or a therapist trained in techniques designed to develop the ability to integrate visual and auditory inputs to recognize emotions, in combination with electrical and/or magnetic cortical stimulation. This stimulation can be targeted at specific cortical regions involved in processing faces and/or voices in normal subjects, including the right superior temporal sulcus (Brodmann area 22), and/or the temporal pole (Brodmann area 38). These areas are expected to be responsible for sensory integration and are shown in FIGS. 21A and 21B. FIG. 21A is a frontal view of the brain, with the right side cut away to illustrate activation peaks at the superior temporal sulcus. FIG. 21B illustrates lateral views of the brain for a control group and an autistic group, and illustrates active areas in the control group, which are generally inactive for autistic patients. Information presented in FIGS. 21A-21B is based on results presented by M. Zilbovicius et al. (2006) Rev. Bras Psiquiatr 28 (Supl 1): S21-S28.

The training session can follow the same general procedure as described above in the training to recognize emotion. However, therapy for enhanced multimodal integration may be somewhat more complex than that associated with unimodal training because patients are subjected to both unimodal and bimodal stimuli. A representative type of therapy trial will determine if the patient more accurately identifies consistent but somewhat ambiguous emotions from the face and voice together than from either modality alone.

In a representative therapy regimen, the patient is instructed to watch Baldi's face, simultaneously listen to his voice, and indicate which emotion was shown given both the face and the voice. In a particular embodiment, only consistent pairings will be presented—that is only a surprised voice will be paired with a surprised face, and so on for the remaining emotions. A 200 ms beep or other signal can be presented prior to presenting the test stimulus to indicate the start of each trial. Following the test stimulus, the patient can be presented (e.g., at a computer screen) with response choices, and can respond by activating an appropriate button labeled "happy," "angry," "surprised," or "fearful" using a mouse, touch screen or other input device. The system can then process the response and provide an indication of the correct emotion. The emotion stimulus can be repeated along with a description of the emotion. To keep the patient engaged, additional feedback can be given for correct responses in the form of "stickers" and verbal praise given by Baldi. Training can continue (in one or more sessions) at least until the patient's performance shows the normal skill in recognizing emotion in the face and voice. Some overtraining may also be provided to achieve enhanced retention.

Example: Communication

In this example, a child or other patient is assessed as positive on DSM IV 2: (qualitative impairments in communication) as manifested by a delay in, or total lack of, the development of spoken language, not accompanied by an attempt to compensate through alternative modes of communication, such as gesture or mime. A representative assessment (e.g., using the techniques described further below) can identify (e.g., pinpoint) the deficit as associated with either or both of two independent processes: hypo- or hypersensitivity of speech inputs, and/or the inappropriate sensory integration of the speech inputs.

Speech perception refers generally to the process of imposing a meaningful perceptual experience on an otherwise meaningless speech input (Massaro, 1998). There is now a large body of evidence indicating that multiple sources of information are available to support the perception, identification, and interpretation of spoken language (Massaro, 1998). Normal or typical language processing involves the evaluation and integration of these multiple sources of information. An autistic child with qualitative impairments in communication can be hypo- or hypersensitive to the inputs, and/or can fail to integrate the sources of information. The language assessment is illustrated below in the context of face-to-face communication.

In normal subjects, speech perception is a bimodal process, influenced by both the sight and sound of the speaker (Massaro, 1998). Experiments have shown that subjects of all ages are highly influenced by both the face and the voice when perceiving speech and understanding language (Massaro, 1998). Research has repeatedly shown that pairing somewhat noisy auditory speech with visual speech from the face produces a percept that is more accurate and less ambiguous, compared to results when presenting either of these modalities alone.

Children with autism might not show similar results for any of at least two possible reasons. First, autistic children may have a problem with initially processing the auditory and visual speech. They may have difficulty perceiving and interpreting the subtle auditory characteristics that distinguish the unique segments in a given language. For example, the auditory difference between "b" and "d" is a change in frequency of the second formant at the onset of the sound. For whatever reason(s), autistic children may not resolve and use this information as efficiently as normally developing children. In addition, children with autism are often known to have some difficulty reading facial expressions (as discussed above) and therefore they may also have difficulty lip reading the visible speech. The visual difference between "b" and "d" is that the mouth is closed at the onset of "b" but open at the onset of "d", and autistic children might have difficulty seeing and utilizing this distinguishing cue.

Second, independently of how well they process the separate auditory and visual modalities, children with autism may have a deficit in performing sensory integration of the auditory and visual speech. For example, such an integration process may be dependent upon mirror neurons and these might be dysfunctional in autism (see, e.g., Williams, J. H. G., Massaro, D. W., Peel, N. J., Bosseler, A., & Suddendorf, T. (2004) "Visual-Auditory integration during speech imitation in autism"—Research in Developmental Disabilities, 25, 559-575; and Williams, J. H., Whiten, A., Suddendorf, T., & Perrett, D. I. (2001) "Imitation, mirror neurons and autism"—*Neuroscience and Biobehavior Review*, 25, 287-295). These two potential deficits can be distinguished by examining speechreading (lipreading) ability on its own as well as in the context of the bimodal speech perception task. A similar logic applies to the auditory speech, and the hypo- or hypersensitivity of the child to auditory speech can be distinguished by examining the child's auditory speech perception ability on its own as well as in the context of the bimodal speech perception task.

Because autistic communication dysfunction may result from either or both of the foregoing deficits, assays in accordance with at least some embodiments distinguish between how much information is obtained from a sensory input and how information is integrated from multiple inputs (Massaro, 1998). Within the framework for assessment, systems and methods in accordance with particular embodiments can make a formal distinction between "information" and "information integration." The sources of information from the auditory and visual channels first make contact with the perceiver at a unimodal sensory evaluation stage of processing. "Information" as used in this context can correspond to a reduction in uncertainty provided by each source. For example, the degree of support for each speech alternative from a given modality corresponds to information. Information integration, on the other hand, refers generally to integrating or combining the two sources of information.

Figure 22:
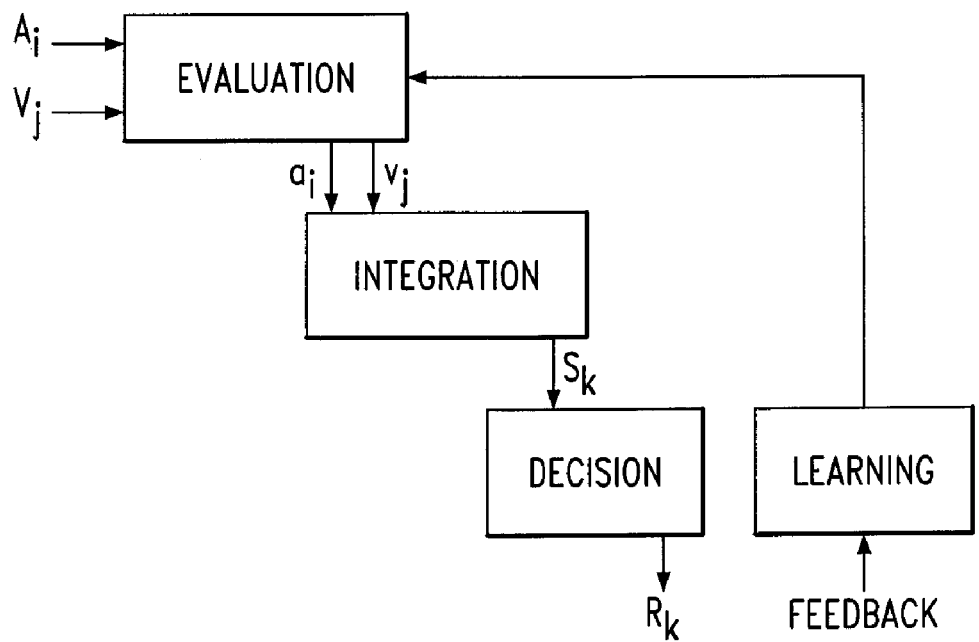
FIG. 22 is a schematic block diagram illustrating representative patient processing of audible and visible speech in a face-to-face dialog for a normal subject.

The foregoing analysis has been formalized in a prototypical pattern recognition model, the Fuzzy Logical Model of Perception (FLMP). This model was developed to account for several important empirical phenomena. The major assumptions upon which the FLMP is based are: 1) multiple sources of information influence speech perception, 2) perceivers have continuous information, not just categorical information, about each source, and 3) the multiple sources are used together in an optimal manner (Massaro, 1998). FIG. 22 illustrates the FLMP's three major operations in pattern recognition: evaluation, integration, and decision. The three perceptual processes are shown to occur left to right in time to illustrate the successive but overlapping processing sequence. These processes make use of prototypes stored in long-term memory. In this hypothetical situation given face-to-face dialog, the evaluation process transforms these sources of information into psychological values, which are then integrated to give an overall degree of support for each speech alternative. The implicit decision operation maps the outputs of integration into some interpretation, which in behavioral experiments can take the form of a discrete decision or a rating of the degree to which the alternative is likely.

As shown in FIG. 22, the sources of information are represented by uppercase letters. Auditory information is represented by $A_i$ and visual information by $V_j$. The evaluation process transforms these sources of information into psychological values (indicated by lowercase letters $a_i$ and $v_j$). These sources are then integrated to give an overall degree of support, $s_k$, for each speech alternative k, which could be as small as a speech segment or as large as an utterance interpretation. The decision operation maps the outputs of integration into some response alternative, $R_k$. The response can take the form of a discrete decision or a rating of the degree to which the alternative is likely. The learning process is also included in FIG. 22. Feedback at the learning stage is assumed to tune the psychological values of the sources of information used by the evaluation process.

Differences between the perceptual and learning processes are also shown schematically in FIG. 22. Perception is generally a feed-forward process in the sense that processing outcomes at a later stage do not feedback and influence earlier stages. Similarly, top-down contextual effects generally do not modify bottom-up perceptual processes. Feedback after perception is assumed to tune the prototypical values of the features used by the evaluation process.

A representative assay, as implemented in accordance with the foregoing framework, allows the practitioner to distinguish information from information integration. A particular embodiment includes independently manipulating two sources of information in an expanded factorial design. It allows an assessment of the influence of the many potentially functional cues, and whether or how these cues are combined to achieve speech perception (see Massaro, 1998). This systematic variation of the properties of the speech signal and quantitative analyses test how different sensory sources of information are perceived and whether or not they are integrated.

Figure 23:
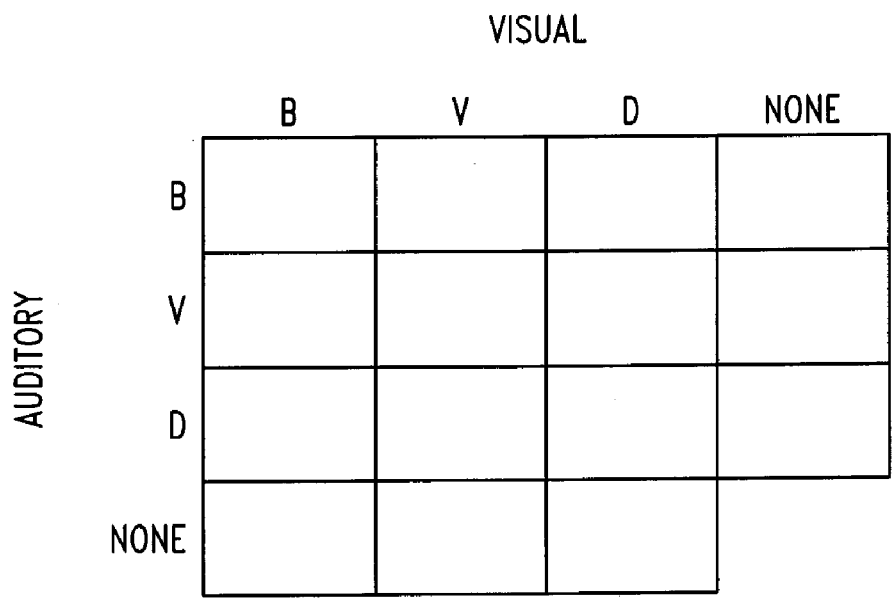
FIG. 23 illustrates an expanded factorial design for three auditory speech categories and three visible speech categories that can be used for patient assessment and/or treatment in accordance with a particular embodiment.

A representative assay uses a so-called expanded factorial design illustrated in FIG. 23. Stimuli can be presented by the computer-animated talking head, Baldi, described previously. Baldi's speech and emotion can be generated by a parametrically controlled polygon topology (Massaro, 1998). An advantage of using the computer-animated talking head is that the stimuli presented by the head can be precisely controlled and replicated over multiple trials. Baldi can mimic natural speech, by incorporating coarticulation and being "trained" by natural speech measurements to accurately duplicate natural speech (Massaro, 1998; Massaro et al., "A multilingual embodied conversational agent"—in R. H. Sprague (Ed.) Proceedings of 38th Annual Hawaii International Conference on Systems Science (HICCS), 2005). The stimuli can include the consonant-vowel (CV) syllables "bi", "vi", and "di". The synthetic visible speech is controlled and aligned with the synthetic audible speech to produce a realistic simulation of a speaking person.

As shown in FIG. 23, the synthetic auditory and visual stimuli are presented unimodally and bimodally in an expanded factorial combination, giving a total of fifteen conditions. There are three auditory conditions, three visual conditions and accordingly nine bimodal conditions. In a representative analysis, each of the fifteen total conditions is sampled randomly without replacement in a block of trials.

The set of fifteen stimuli can be repeated a number of times for each patient. The results can be analyzed to determine how the sensory sources of information are perceived and whether or not they are integrated. This outcome can then be used to determine, at least in part, a rehabilitative therapy regimen. For example, in some cases, the practitioner may determine that the patient is capable of perceiving auditory speech but is not able to lipread, and accordingly fails to obtain the benefit of visual cues in face-to-face communications. In such cases, the patient can be trained to lipread syllables while cortical stimulation is applied to the appropriate brain area.

As discussed previously, much of the visual processing of facial expression in normal subjects is located in the fusiform face area (FFA) located on the fusiform gyrus (FG). In addition, language processing is predominantly carried out in the left hemisphere in normal subjects. Thus, the practitioner can select the left FFA as a cortical target area for facilitating lip reading in ASD patients.

During a treatment regimen in accordance with a particular embodiment, the patient is instructed to watch Baldi and indicate the syllable that was spoken. A 200 ms beep or other suitable signal is presented prior to the presentation of the test stimulus to indicate the start of each trial. Following the test presentation, response buttons or other suitable input devices are presented to the patient, e.g., in the upper left hand corner of a computer-driven display. The patient responds by selecting "B," "V," or "D," using a mouse, touch screen or appropriately labeled button. To keep the patient engaged, feedback can be given for correct responses in the form of "stickers" and verbal praise given by Baldi. Treatment including the foregoing adjunctive behavior in combination with cortical stimulation can continue until the patient's performance shows the normal skill in lipreading.

Once the patient's lipreading ability is established and/or improved, the practitioner can repeat the original assay to evaluate the ability of the patient to integrate the auditory and visual components of speech. If a deficit in sensory integration is identified during the assay, the practitioner can initiate a therapy regimen that includes one or more corrective treatments that emphasize sensory integration, in combination with cortical stimulation. The behavioral therapy can follow the same general procedure as described previously in the content of the multimodal sensory integration training.

The target neural population stimulated to facilitate sensory integration for enhanced communication can include the left superior temporal sulcus (Brodmann area 22), and in particular embodiments, Wernicke's area located on the more posterior aspect of the STS. Two other adjoining areas, the angular gyrus (Brodmann area 39) and supramarginal gyrus (Brodmann area 40), are also typically involved with sensory integration of speech. Accordingly, stimulating these areas may also facilitate sensory integration development in specific ASD patients.

Example: Use of Contextual Information in Speech Perception

One of the landmark abilities of humans is to benefit from the situational context of social and communication encounters. Our often seamless ability to understand language, for example, is highly dependent on knowing the language being spoken. A common impression is that foreign languages are spoken very rapidly without pauses. In fact, all languages are spoken at roughly the same rate with very few pauses between successive words. We tend to "hear" pauses because of our knowledge of the words.

One important measure of autistic behavior is the extent to which the patient uses context. A representative diagnostic/therapeutic regimen includes assaying the patient's ability to use context in one or more of several ways, and then developing therapies that include teaching the use of context, in combination with stimulating the appropriate brain area. One test includes measuring lexical influences in speech perception by manipulating the segmental information in a speech item and the lexical context. The initial speech segment will be synthesized to vary the degree to which it sounds like "d" or "t." The voice onset time or the time between the initial burst of the sound and the onset of vocal cord vibration will be varied in small steps to produce a set of test stimuli between "d" and "t." This speech segment will be placed as the initial consonant before the contexts "urf" and "irt." The consonant "t" makes a word in the context urf whereas "d" makes a word in the context "irt." During the test, these sound combinations are randomly presented to listeners who are asked to indicate whether the initial segment was a "d" or "t." The judgments of normally functioning listeners are influenced by both the initial speech segment and the context. The results indicate that the likelihood of a "t" judgment increases as the voice onset time is lengthened. In addition, "t" judgments are more frequent in the context "urf" than "irt," in agreement with an influence of lexical context. The influence of lexical context is greatest at the more ambiguous levels of initial segment, as predicted by an integration model (Massaro, 1998).

Using the foregoing technique, a practitioner can assess whether and to what extent a patient uses the initial segment information and the context information, and whether and to what extent these two sources are integrated. The outcome of the assessment can determine, at least in part, an appropriate therapy, analogous to those described previously in the contexts of social interaction and communication.

In particular embodiments, the cortical target stimulated to facilitate the use of contextual information in speech perception is the left superior temporal gyrus (Brodmann area 42) and in other embodiments, other areas may be stimulated, e.g., if such areas are determined to play a role in the patient's use of contextual information.

Example: Influence of Context on Comprehension

Many children with autism do acquire language and learn to read but they continue to have difficulty taking into account context. In reading, for example, their pronunciation and therefore interpretation of homographs is not appropriately constrained by context. (Snowing, M. & Frith, U. (1986) "Comprehension in "hyperlexic" readers," Journal of Experimental Child Psychology, 42, 392-415). For example, consider the sentences: "I live just across the lake" and "I saw a live animal in the backyard." Typically developing readers will pronounce these two versions of "live" differently and appropriately in the two contexts. Autistic patients can be assessed in a test that evaluates how homographs such as "live," "bow," and "lead" are read in context. If a patient shows insensitivity to context in his or her reading, a treatment regimen can be related to teach these contextual constraints while the appropriate brain area is stimulated. For example, in one type of training session, the patient will see a written text simultaneously with an aural reading of the text. As the text is read, the written word that is being spoken will be highlighted, so the patient can follow along silently reading the text as it is being spoken. In this way, the patient can be trained to associate the appropriate reading of a word, given the constraining context. In addition to these training trials, the patient can be tested by reading aloud the same texts and new texts. The cortical target stimulated to facilitate the influence of context on comprehension can include the left superior temporal gyrus (Brodmann area 22) and/or other suitable areas.

Example: Early Visual and Auditory Integration

The tasks described to this point have involved fairly sophisticated processing such as recognizing emotion, speech, words, or language comprehension. In some cases, patients may have deficits in the early stages of multisensory processing. In a well-known illusion, sound can induce a visual flash illusion (Shams, L, Kamitani Y, Shimojo, S (2000) "What you see is what you hear," Nature, 408, 788). If a short flash is presented, people correctly report a single flash. If the same flash is presented with two short sounds, the single flash is perceived as two. This task can be used to assess to what extent an autistic patient has deficits in integration of auditory and visual information. Autistic children can be tested in this task to see if they experience the illusion. If they do not, then an appropriate training regimen can be initiated with stimulation of the appropriate brain area. The cortical targets stimulated to facilitate early visual and auditory Integration can include Brodmann areas 37 and 39.

Example: Early Visual and Tactile Integration

A task similar to that described above includes interactions between visual information with somatosensory information (Violentyev A, Shimojo S, Shams L. (2005) "Touch-induced visual illusion," Neuroreport, Vol. 16. No. 10 (13 Jul. 2005), pp. 1107-1110). For example, people have reported seeing two flashes when a single flash is paired concurrently with two brief tactile stimuli. An assay and treatment regimen generally similar to that described above (with tactile stimulation substituted for auditory stimulation) can accordingly be administered to the patient. The cortical target stimulated to facilitate early visual and tactile integration can include Brodmann area 7.

Although the proposed tests and training regimens have been described in the domain of autism, they are equally applicable to similar symptoms in other disabilities like dyslexia, speech language impairment, ADHD, and learning delays/disabilities.

From the foregoing, it will be appreciated that specific embodiments of the disclosure have been described herein for purposes of illustration, but that various modifications may be made without deviating from the disclosure. For example, many of the foregoing tests and training regimens were described in the context of autism. In other embodiments, identical and/or generally similar tests and training regimens may be applicable to patients having similar symptoms, but other disabilities. Such disabilities can include dyslexia, speech language impairment, ADHD, and/or learning delays/disabilities. As was also discussed above, many of the stimulation techniques include stimulation via electrodes placed at or above the cortical surface of the brain, but in other embodiments, suitable stimulation may be applied by electrodes positioned beneath the cortical surface (e.g., penetrating electrodes) and/or by signal delivery devices placed outside the patient skull (e.g., transcranial magnetic stimulation devices or transcranial direct current stimulation devices). The "stimulation" signals can have inhibitory affects, excitatory affects, and/or affects that enhance neuroplasticity.

Certain aspects of the disclosure described in the context of particular embodiments may be combined or eliminated in other embodiments. For example, techniques and/or devices described in the context of addressing particular patient symptoms may be adjusted to address other symptoms. In a particular example, the electrodes shown in FIG. 11 may be placed at other locations of the brain to address other patient dysfunctions. In general, it is expected that the foregoing techniques can more accurately identify target neural populations, and thus provide more effective treatment. While advantages associated with certain embodiments of the disclosure have been described in the context of those embodiments, other embodiments may also exhibit such advantages, and not all embodiments need necessarily exhibit such advantages to fall within the scope of the disclosure. Accordingly, aspects of the invention may cover embodiments not expressly shown or described herein.

We claim:

1. A method for treating a patient dysfunction, comprising:
   determining that the patient suffers from an autism spectrum disorder;
   based at least in part on the determination that the patient suffers from an autism spectrum disorder, selecting a target neural population of the patient's brain, wherein the target neural population is selected from the group consisting of amygdala, superior temporal sulcus and Brodmann area 36;

applying electromagnetic signals to the target neural population; and administering a training program to the patient to train the patient to recognize expressions of facial emotion thereby promoting cortical organization of the patient's brain by administering a behavioral adjunctive therapy in conjunction with delivering electromagnetic signals.

2. The method of claim 1, further comprising identifying the target neural population as being hypoactive, and wherein delivering the electromagnetic signals includes increasing the activation level of the target neural population.

3. The method of claim 2 wherein delivering the electromagnetic signals includes delivering the electromagnetic signals at a frequency greater than about 5 Hz.

4. The method of claim 1, further comprising identifying the target neural population as being hyperactive, and wherein delivering the electromagnetic signals includes decreasing the activation level of the target neural population.

5. The method of claim 4 wherein delivering the electromagnetic signals includes delivering the electromagnetic signals at a frequency of less than 5 Hz.

6. The method of claim 1 wherein delivering the electromagnetic signals includes delivering the electromagnetic signals from an implanted electrode positioned beneath the patient's skull and external to a cortical surface of the patient's brain.

7. The method of claim 1 wherein delivering the electromagnetic signals includes delivering the electromagnetic signals from a site external to the patient's skull.

8. The method of claim 7 wherein determining that the patient suffers from an autism spectrum disorder includes determining that a child patient suffers from an autism spectrum disorder, and wherein delivering the electromagnetic signals includes delivering the electromagnetic signals via transcranial magnetic stimulation.

9. The method of claim 1 wherein delivering the electromagnetic signals includes delivering the electromagnetic signals from an implanted electrode positioned beneath a cortical surface of the patient's brain.

* * * * *